United States Patent [19]

Klotz

[11] 4,405,504

[45] * Sep. 20, 1983

[54] CATALYTIC COMPOSITIONS

[75] Inventor: Marvin R. Klotz, Batavia, Ill.

[73] Assignee: Standard Oil Company (Indiana), Chicago, Ill.

[*] Notice: The portion of the term of this patent subsequent to Nov. 10, 1998, has been disclaimed.

[21] Appl. No.: 281,839

[22] Filed: Jul. 9, 1981

Related U.S. Application Data

[63] Continuation-in-part of Ser. No. 69,236, Aug. 23, 1979, Pat. No. 4,299,808, which is a continuation-in-part of Ser. No. 927,843, Jul. 25, 1978, abandoned, which is a continuation of Ser. No. 733,269, Oct. 18, 1976, abandoned.

[51] Int. Cl.³ .......................... B01J 29/00; B01J 29/04
[52] U.S. Cl. ..................................... 423/458; 423/326
[58] Field of Search .................. 252/458, 431 N, 454; 423/326, 332

[56] References Cited

U.S. PATENT DOCUMENTS 3,702,886 11/1972 Argauer et al. ...................... 423/328
3,709,979 1/1973 Chu .................................... 423/329
3,832,449 8/1974 Rosinski et al. ...................... 423/329
4,299,808 11/1981 Klotz ................................... 423/331

Primary Examiner—Edward J. Meros
Attorney, Agent, or Firm—James L. Wilson; William T. McClain; William H. Magidson

[57] ABSTRACT

There is provided a catalytic composition which comprises a mixture of a crystalline chromosilicate and an oxide of chromium, said catalytic composition providing a specific X-ray diffraction pattern and having the following composition in terms of mole ratios of oxides:

$0.9 \pm 0.2$ $M_{2/n}O:Cr_2O_3:YSiO_2:ZH_2O$, wherein M is at least one cation having a valence of n, Y is a value within the range of about 4 to about 500, and Z is a value within the range of about 0 to about 160. There is also provided a method for preparing such a catalytic composition.

There is provided a process for the conversion of a hydrocarbon stream which comprises contacting said stream at conversion conditions with the above catalytic composition. In addition, there is provided a process for the isomerization of a xylene feed which comprises contacting said feed at isomerization conditions with the above catalytic composition.

16 Claims, 1 Drawing Figure

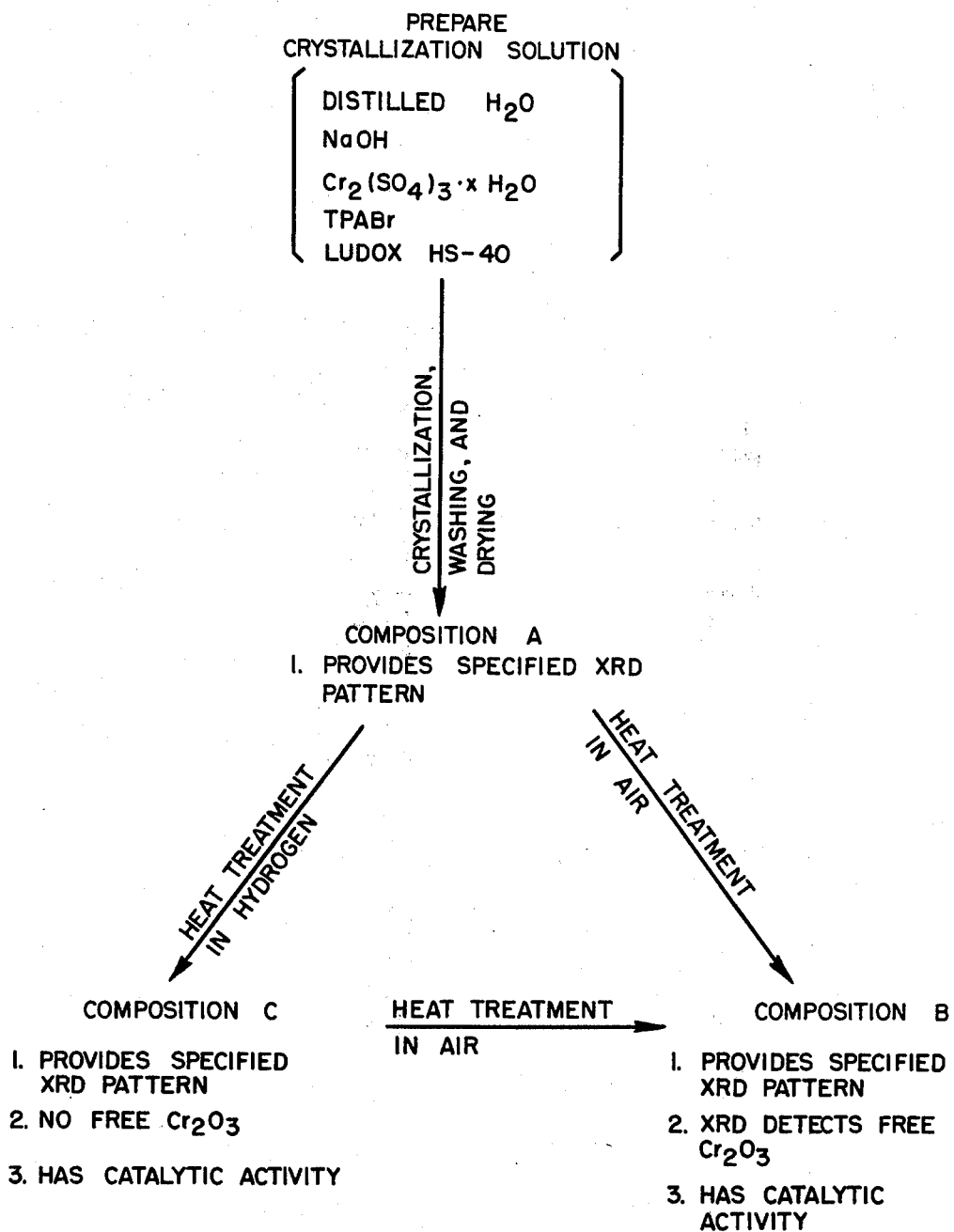

CATALYTIC COMPOSITIONS

CROSS REFERENCE TO RELATED APPLICATIONS

This application is a continuation-in-part application of co-pending application U.S. Ser. No. 69,236, filed in the U.S. Patent and Trademark Office on Aug. 23, 1979 and now U.S. Pat. No. 4,299,808, which co-pending application is a continuation-in-part application of U.S. Ser. No. 927,843, filed in the U.S. Patent and Trademark Office on July 25, 1978, and now abandoned. U.S. Ser. No. 927,843 is, in turn, a continuation application of U.S. Ser. No. 733,269, which was filed in the U.S. Patent and Trademark Office on Oct. 18, 1976, and is now abandoned.

Two applications are being filed concurrently with this application. These are U.S. Ser. Nos. 281,828 and 281,840.

U.S. Ser. No. 281,840 is directed to AMS-1Cr crystalline chromosilicates; a catalytic composition comprising a molecular sieve-containing component and a porous refractory inorganic oxide, the molecular sieve-containing component comprising a crystalline chromosilicate and an oxide of chromium; a method for preparing the catalytic composition; and processes employing that catalytic composition.

U.S. Ser. No. 281,828 is directed to AMS-1Cr crystalline chromosilicates; a catalytic composition comprising a crystalline chromosilicate and a porous refractory inorganic oxide; a method for preparing the catalytic composition; and processes employing that catalytic composition.

BACKGROUND OF THE INVENTION

1. Field of the Invention

This invention relates to novel crystalline chromosilicates and to their use. More particularly, this invention relates to catalytic compositions containing novel chromosilicate crystalline molecular sieve materials having catalytic properties and to various hydrocarbon conversion processes using such catalytic compositions. The field of art can, in part, be found in U.S. Patent Class 423-326, 252-458 and 260-668.

2. Description of the Prior Art

Zeolitic materials, both natural and synthetic, have been demonstrated in the past to have catalytic capabilities for many hydrocarbon processes. Certain zeolitic materials are ordered porous crystalline aluminosilicates having a definite structure with large and small cavities interconnected by channels. The cavities and channels throughout the crystalline material are generally uniform in size, allowing certain hydrocarbons to be selectively adsorbed giving one of the practical utilities to these materials. Consequently, these materials in many instances have come to be classified in the art as molecular sieves and are utilized, in addition to the adsorptive selective processes, for certain catalytic properties. The catalytic properties of these materials are also affected in some instances by the size of the molecules which are allowed selectively to penetrate the crystal structure presumably to be contacted with active catalytic sites within the ordered structure of these materials.

Generally the term "molecular sieve" includes a wide variety of positive ion containing crystalline materials of both natural and synthetic varieties. They are generally characterized as crystalline aluminosilicates, although other crystalline materials are included in the broad definition. The crystalline aluminosilicates are made up of networks of tetrahedra of $SiO_4$ and $AlO_4$ moieties in which the silicon and aluminum atoms are cross-linked by the sharing of oxygen atoms. The electrovalence of the aluminum atom is balanced by the use of a positive ion, for example, alkali metals or alkaline earth metals.

Prior art developments have resulted in the formation of many synthetic crystalline materials. Crystalline aluminosilicates are the most prevalent and, as described in the patent literature and in the published journals, are designated by letters or other convenient symbols. Exemplary of these materials are Zeolite A (U.S. Pat. No. 2,882,234), Zeolite X (U.S. Pat. No. 2,882,244), Zeolite Y (U.S. Pat. No. 3,130,007), Zeolite ZSM-5 (U.S. Pat. No. 3,702,886), Zeolite ZSM-11 (U.S. Pat. No. 3,709,979), Zeolite ZSM-12 (U.S. Pat. No. 3,832,449), and others.

Especially relevant art is the above U.S. Pat. No. 3,702,886, claiming the crystalline aluminosilicate Zeolite ZSM-5 and the method for making the same. This patent is limited to the production of a zeolite wherein aluminum or gallium oxides are present in the crystalline structure along with silicon or germanium oxides. A specific ratio of the latter to the former are reacted to produce a class of zeolites designated ZSM-5 all limited to crystalline alumino- or gallo-silicates or germanates and having a specified X-ray diffraction pattern. The above ZSM-11 and ZSM-12 patents are similarly limited to crystalline alumino- or gallo-silicates or germanates also having specified X-ray diffraction patterns.

Manufacture of the ZSM materials utilizes a mixed base system in which materials such as sodium aluminate and a silica-containing material are mixed together with sodium hydroxide and an organic base, such as tetra-propylammonium hydroxide and tetra-propylammonium bromide, under specified reaction conditions to form the crystalline aluminosilicate material having a specific X-ray diffraction pattern.

Other relevant art includes U.S. Pat. Nos. 3,329,480 and 3,329,481, which relate to "zircono-silicates" and "titano-silicates" respectively.

The present invention, however, relates to a novel family of stable synthetic crystalline materials characterized as chromosilicates identified as AMS-1Cr and having a specified X-ray diffraction pattern and to catalytic compositions containing such crystalline chromosilicates.

SUMMARY OF THE INVENTION

The present invention relates to a novel synthesis AMS-1Cr crystalline chromosilicate, to novel catalytic compositions which contain such crystalline chromosilicates, and to process uses of such catalytic compositions. The family of AMS-1Cr crystalline chromosilicate materials has a specified X-ray diffraction pattern, as is shown hereinafter.

Broadly, there is provided a catalytic composition which comprises a mixture of a crystalline chromosilicate and an oxide of chromium, said catalytic composition providing an X-ray diffraction pattern comprising the following X-ray diffraction lines and assigned strengths:

| Interplanar Spacing d, Å | Assigned Strengths |
| --- | --- |
| 11.14 ± 0.2 | M |
| 9.89 ± 0.2 | VS |
| 3.85 ± 0.07 | MS |
| 3.81 ± 0.07 | M |
| 3.72 ± 0.05 | M |
| 3.63 ± 0.05 | M |
| 2.67 ± 0.02 | M |
| 2.48 ± 0.02 | M | and having the following composition in terms of mole ratios of oxides:

$$0.9 \pm 0.2 M_{2/n}O : Cr_2O_3 : YSiO_2 : ZH_2O,$$

wherein M is at least one cation having a valence of n, Y is a value within the range of about 4 to about 500, and Z is a value within the range of 0 to about 160.

There is also provided a method for preparing this catalytic composition, which method comprises: (1) preparing a mixture containing an oxide of silicon, a compound of chromium, a hydroxide of an alkali metal or an alkaline earth metal, an alkylammonium cation or a precursor of an alkylammonium cation, and water; (2) maintaining said mixture at suitable reaction conditions to effect formation of a crystalline material, said reaction conditions comprising a reaction temperature within the range of about 25° C. to about 300° C., a pressure of at least the vapor pressure of water at the reaction temperature, and a reaction time that is sufficient to effect crystallization to crystals of said chromosilicate; (3) washing and drying said crystals; and (4) calcining the resulting product in an oxygen-containing atmosphere at a temperature within the range of about 800° F. (427° C.) to about 1,700° F. (927° C.).

In addition, there is provided a process for the conversion of a hydrocarbon stream, which process comprises contacting said stream at conversion conditions with the catalytic composition described hereinabove.

Furthermore, there is provided a process for the catalytic isomerization of a xylene feed, which process comprises contacting said feed at isomerization conditions with the catalytic composition described hereinabove.

BRIEF DESCRIPTION OF THE ACCOMPANYING DRAWING

The accompanying FIGURE depicts the relationships between three chromosilicate compositions, identified as Composition A (as prepared but without a high-temperature treatment). Composition B (heat-treated in an oxygen-containing atmosphere), and Composition C (heat-treated in a hydrogen-containing atmosphere).

DESCRIPTION AND SPECIFIC EMBODIMENTS

The present invention relates to a novel synthetic crystalline molecular sieve material, a crystalline chromosilicate, a catalytic composition containing such chromosilicate, and processes employing such catalytic composition.

The family of such crystalline chromosilicate materials, which are identified as AMS-1Cr chromosilicates, has a particular X-ray diffraction pattern, as is shown in the various tables hereinafter.

Such crystalline chromosilicates can be characterized generally in terms of the mole ratios of oxides as shown in Expression I:

$$0.9 \pm 0.2 M_{2/n}O : Cr_2O_3 : YSiO_2 : ZH_2O \quad (I),$$

wherein M is at least one cation having a valence of n, Y is a value within the range of about 4 to about 500, and Z represents the water present in such material and has a value within the range of 0 to about 160, or more.

In another instance, the claimed AMS-1Cr crystalline chromosilicate can be represented in terms of mole ratios of oxides for the crystalline material which has not yet been activated at a high temperature as is shown hereinafter in Expression II:

$$0.9 \pm 0.2 [WR_2O + [1-W]M_{2/n}O] : Cr_2O_3 : YSiO_2 : ZH_2O \quad (II),$$

wherein R is tetrapropylammonium cation, M is at least one cation having a valence of n, Y is a value within the range of about 4 to about 500, Z is a value within the range of about 0 to about 160, and W is a value that is greater than or equal to 0 and less than or equal to 1.

The original cation, that is M in the above formulations, can be replaced in accordance with techniques well known in the art, at least in part by ion exchange with other cations. Preferred replacing cations include tetraalkylammonium cations, metal ions, ammonium ions, hydrogen ions, and mixtures of the above. Particularly preferred cations are those which render the AMS-1Cr crystalline chromosilicate catalytically active, especially for hydrocarbon conversion. These materials include hydrogen, ammonium ions, rare earth metals, aluminum, metals of Groups IB, IIB and VIII of the Periodic Table of Elements, noble metals, manganese, etc., and other catalytically active materials and metals known to the art. Reference is made to the Periodic Table of Elements on page 628 of WEBSTER'S SEVENTH NEW COLLEGIATE DICTIONARY, G. & C. Merriam Company, Springfield, Mass., U.S.A. (1963). The catalytically active components can be present anywhere from about 0.05 to about 25 weight percent of the AMS-1Cr crystalline chromosilicate.

Members of the family of AMS-1Cr crystalline chromosilicates possess specified and distinguishing crystalline structures.

X-ray diffraction patterns of various samples of AMS-1Cr crystalline chromosilicates were obtained by the following method: A Phillips instrument which utilized copper K alpha radiation was employed. The theta angles were recorded on a strip chart using a proportional counter. The theta values recorded were converted to interplanar spacing values in Angstroms (Å) using the Bragg equation. The relative intensities (relative peak heights) were calculated as (100 I/I$_o$), where I$_o$ is the intensity of the strongest recorded peak and I is the value actually read for the particular interplanar spacing.

For ease of reporting the results, the relative intensities (relative peak heights) were arbitrarily assigned the following values:

| Relative Peak Height | Assigned Strength |
| --- | --- |
| less than 10 | VW (very weak) |
| 10–19 | W (weak) |
| 20–39 | M (medium) |
| 40–70 | MS (medium strong) |
| greater than 70 | VS (very strong) |

The X-ray diffraction pattern showing the following significant lines in the indicated relative intensities (relative peak heights) and assigned strengths for the AMS-1Cr crystalline chromosilicate is shown in Table I below:

TABLE I

| Interplanar Spacing d, Å | Relative Intensity $I/I_o$ | Assigned Strength |
|---|---|---|
| 11.04 ± 0.2 | 100 | VS |
| 10.04 ± 0.2 | 68 | MS |
| 7.49 ± 0.2 | 2 | VW |
| 6.70 ± 0.2 | 6 | VW |
| 6.37 ± 0.1 | 10 | W |
| 5.98 ± 0.1 | 20 | M |
| 5.67 ± 0.1 | 9 | VW |
| 5.53 ± 0.1 | 12 | W |
| 5.34 ± 0.1 | 2 | VW |
| 4.98 ± 0.1 | 10 | W |
| 4.62 ± 0.08 | 5 | VW |
| 4.35 ± 0.08 | 8 | VW |
| 4.27 ± 0.08 | 12 | W |
| 4.09 ± 0.08 | 2 | VW |
| 4.02 ± 0.08 | 6 | VW |
| 3.85 ± 0.07 | 85 | VS |
| 3.72 ± 0.05 | 53 | MS |
| 3.64 ± 0.05 | 36 | M |
| 3.42 ± 0.05 | 10 | W |
| 3.30 ± 0.05 | 10 | W |
| 3.24 ± 0.05 | 4 | VW |
| 3.12 ± 0.05 | 1 | VW |
| 3.05 ± 0.03 | 8 | VW |
| 2.98 ± 0.02 | 16 | W |
| 2.96 ± 0.02 | 11 | W |
| 2.85 ± 0.02 | 2 | VW |
| 2.78 ± 0.02 | 2 | VW |
| 2.74 ± 0.02 | 4 | VW |
| 2.66 ± 0.02 | 23 | M |
| 2.59 ± 0.02 | 3 | VW |
| 2.55 ± 0.02 | 2 | VW |
| 2.48 ± 0.02 | 26 | M |
| 2.39 ± 0.02 | 4 | VW |
| 2.26 ± 0.02 | 2 | VW |
| 2.17 ± 0.02 | 9 | VW |
| 2.00 ± 0.02 | 10 | W |
| 1.99 ± 0.02 | 11 | W |

The above X-ray pattern is characteristic of the AMS-1Cr crystalline chromosilicate having the oxide mole formula described in Expression I, which chromosilicate has been calcined at 1,100° F., wherein the tetraalkylammonium ion has been removed from the system by the calcination procedure.

In the following Table, the stronger interplanar spacings are summarized for the AMS-1Cr chromosilicate from Table I above:

TABLE II

| Interplanar Spacing d, Å | Assigned Strength |
|---|---|
| 11.04 ± 0.2 | VS |
| 10.04 ± 0.2 | MS |
| 3.85 ± 0.07 | VS |
| 3.72 ± 0.05 | MS |
| 3.64 ± 0.05 | M |
| 2.66 ± 0.02 | M |
| 2.48 ± 0.02 | M |

Such a calcination is now known to effect the removal of chromium oxides from the framework of the AMS-1Cr crystalline chromosilicate molecular sieve, which oxides can be identified by X-ray diffraction. The X-ray diffraction pattern of $Cr_2O_3$ includes an interplanar spacing of 2.67 Å at a relative intensity of 100; an interplanar spacing of 2.48 Å at a relative intensity of 95; an interplanar spacing of 1.67 Å at a relative intensity of 90; an interplanar spacing of 3.63 Å at a relative intensity of 75; and an interplanar spacing of 2.17 Å at a relative intensity of 40. Chromium oxides were not detected by the X-ray diffraction technique until the chromium concentration with the sieve framework had been increased sufficiently to make the chromium oxide reflections obvious. It is to be noted that the ability to detect chromium oxide is only semi-quantitative, since pretreatment variables in preparation and calcination exist and since the major $Cr_2O_3$ reflections are identical in interplanar spacing (d) with some of the X-ray reflections provided by the crystalline chromosilicate material.

In instances in which the AMS-1Cr crystalline chromosilicate is analyzed under an X-ray diffraction pattern in an as-produced state (prior to high temperature treatment but after some reasonable amount of drying has taken place), the crystalline chromosilicate generally is characterized in Expression II above and has an X-ray diffraction pattern showing the following significant lines and assigned strengths:

TABLE III

| Interplanar Spacing d, Å | Assigned Strength |
|---|---|
| 11.04 ± 0.2 | S |
| 10.04 ± 0.2 | S |
| 9.71 ± 0.2 | W |
| 8.84 ± 0.2 | VW |
| 8.34 ± 0.2 | VW |
| 7.89 ± 0.2 | VW |
| 7.37 ± 0.2 | W |
| 7.02 ± 0.2 | VW |
| 6.70 ± 0.2 | VW |
| 6.32 ± 0.1 | W |
| 5.98 ± 0.1 | W |
| 5.68 ± 0.1 | W |
| 5.53 ± 0.1 | W |
| 5.34 ± 0.1 | VW |
| 5.09 ± 0.1 | VW |
| 4.98 ± 0.1 | W |
| 4.60 ± 0.08 | W |
| 4.35 ± 0.08 | W |
| 4.27 ± 0.08 | W |
| 4.07 ± 0.08 | VW |
| 4.00 ± 0.08 | W |
| 3.80 ± 0.07 | VS |
| 3.74 ± 0.05 | M |
| 3.70 ± 0.05 | S |
| 3.64 ± 0.05 | MS |
| 3.46 ± 0.05 | VW |
| 3.42 ± 0.05 | W |
| 3.32 ± 0.05 | W |
| 3.31 ± 0.05 | W |
| 3.30 ± 0.05 | W |
| 3.23 ± 0.05 | VW |
| 3.14 ± 0.05 | VW |
| 3.04 ± 0.03 | W |
| 2.98 ± 0.02 | W |
| 2.94 ± 0.02 | W |
| 2.85 ± 0.02 | VW |
| 2.78 ± 0.02 | VW |
| 2.73 ± 0.02 | W |
| 2.65 ± 0.02 | VW |
| 2.60 ± 0.02 | W |
| 2.56 ± 0.02 | VW |
| 2.51 ± 0.02 | VW |
| 2.48 ± 0.02 | W |
| 2.44 ± 0.02 | VW |
| 2.40 ± 0.02 | VW |
| 2.39 ± 0.02 | W |
| 2.10 ± 0.02 | VW |
| 2.07 ± 0.02 | VW |
| 2.00 ± 0.02 | W |
| 1.996 ± 0.02 | W |
| 1.96 ± 0.02 | VW |
| 1.95 ± 0.02 | W |
| 1.91 ± 0.02 | W |

TABLE III-continued

| Interplanar Spacing d, Å | Assigned Strength |
| --- | --- |
| 1.86 ± 0.02 | W |

Please note that the assigned strengths presented in this Table III and in the following Table IV do not correspond to the intensities that are defined hereinabove for assigned strengths. In these two tables, "S" approximates the defined "MS" in the list of assigned strengths.

In the following Table, the stronger interplanar spacings are summarized for AMS-1Cr crystalline chromosilicate from Table III above:

TABLE IV

| Interplanar Spacing d, Å | Assigned Strength |
| --- | --- |
| 11.04 ± 0.2 | S |
| 10.04 ± 0.2 | S |
| 3.80 ± 0.07 | VS |
| 3.74 ± 0.05 | M |
| 3.70 ± 0.05 | S |
| 3.64 ± 0.05 | MS |

The AMS-1Cr crystalline chromosilicate are useful in the hydrocracking process. They appear to have relatively useful catalytic properties in petroleum refining processes, such as the isomerization of normal-paraffins and naphthenes, the reforming of certain feedstocks, the isomerization of aromatics, especially the isomerization of polyalkyl-substituted aromatics, such as xylenes, hydrodealkylation of aromatics, the disproportionation of aromatics, the alkylation of hydrocarbons, and the dewaxing of hydrocarbon streams. When used as a catalyst in isomerization processes with suitable cations placed on the ion-exchangeable sites (M) within the AMS-1Cr crystalline chromosilicate, reasonably high selectivities for desired isomerizaton take place with feedstocks containing xylenes. In addition, impregnation of the chromosilicate with a metal, such as nickel, will furnish improved isomerization of xylenes. The chromosilicates also possess superior transalkylation and disproportionation activities for aromatics containing ethyl groups.

In a broad embodiment, my invention relates to a crystalline chromosilicate having a composition in terms of oxides as follows:

$$0.9 \pm 0.2[WR_2O + (1-W)M_{2/n}O]:Cr_2O_3:YSiO_2:ZH_2O,$$

wherein R is tetraalkylammonium, M is an alkali metal cation, W is greater than 0 and less than or equal to 1, Y is at least 4, Z is between 0 and about 160 and having the X-ray diffraction pattern substantially as described in Tables III or IV of the specification hereinabove. For the sake of convenience, this embodiment will be identified as the first crystalline chromosilicate. Preferably, Y is a value between about 4 and about 200.

In a more preferred embodiment, W is a value between about 0.7 and about 0.9, Y is a value between about 4 and about 200, and Z is a value between about 0 and about 160.

In another broad embodiment, my invention relates to a crystalline chromosilicate having a composition in terms of mole ratios of oxides as follows:

$$0.9 \pm 0.2 M_{2/n}O:Cr_2O_3:YSiO_2:ZH_2O,$$

wherein M is at least one cation having a valence of n, Y is between 4 and about 500 and Z is between 0 and about 160, said chromosilicate having the X-ray diffraction lines and assigned strength substantially as described in Table I or Table II of the specification. Advantageously, Y is a value between about 4 and about 200.

In a more preferred embodiment, Y is a value within the range of about 4 to about 100. Z can be a value between about 0 and about 40. In an even more preferred embodiment, Y is a value between about 4 and about 40.

Broadly, in accordance with the present invention there is provided a crystalline chromosilicate which comprises a molecular sieve material providing an X-ray diffraction pattern comprising the following X-ray diffraction lines and assigned strengths:

| Interplanar Spacing d, Å | Assigned Strength |
| --- | --- |
| 11.04 ± 0.2 | S |
| 10.04 ± 0.2 | S |
| 3.80 ± 0.07 | VS |
| 3.74 ± 0.05 | M |
| 3.70 ± 0.05 | S |
| 3.64 ± 0.05 | MS | and having the following composition in terms of mole ratios of oxides:

$$0.9 \pm 0.2[WR_2O + (1-W)M_{2/n}O]:Cr_2O_3:YSiO_2:ZH_2O,$$

wherein R is an alkylammonium cation, M is at least one cation having a valence of n, Y is a value within the range of about 4 to about 500, Z is a value within the range of about 0 to about 160, and W is a value that is greater than or equal to 0 and less than or equal to 1. This represents the first crystalline chromosilicate, which is a precursor of a second chromosilicate described hereinbelow. It is contemplated that such chromosilicate precursor can also be prepared without an organic template, such as alkylammonium cation, wherein the value of W in the above expression approaches and is equal to zero.

There is provided a second crystalline chromosilicate, which comprises a molecular sieve material providing an X-ray diffraction pattern comprising the following X-ray diffraction lines and assigned strengths:

| Interplanar Spacing d, Å | Assigned Strength |
| --- | --- |
| 11.15 ± 0.2 | W |
| 9.96 ± 0.2 | VS |
| 5.99 ± 0.1 | VW |
| 5.71 ± 0.1 | VW |
| 4.97 ± 0.1 | W |
| 3.85 ± 0.07 | M |
| 3.82 ± 0.07 | MS |
| 3.75 ± 0.05 | M |
| 3.32 ± 0.05 | VW |
| 1.99 ± 0.02 | W | and having the following composition in terms of mole ratios of oxides:

$$0.9 \pm 0.2\ M_{2/n}O:Cr_2O_3:YSiO_2:ZH_2O,$$

wherein M is at least one cation having a valence of n, Y is within the range of about 4 to about 500, and Z is within the range of 0 to about 160.

The first chromosilicate is a precursor of the second. Also, it is contemplated that for either of the above two crystalline chromosilicates, advantageously, Y is a value within the range of about 4 to about 200.

There is provided a catalytic composition which comprises a mixture of a crystalline chromosilicate and an oxide of chromium, said catalytic composition providing an X-ray diffraction pattern comprising the following X-ray diffraction lines and assigned strengths:

| Interplanar Spacing d, Å | Assigned Strength |
|---|---|
| 11.14 ± 0.2 | M |
| 9.89 ± 0.2 | VS |
| 3.85 ± 0.07 | MS |
| 3.81 ± 0.07 | M |
| 3.72 ± 0.05 | M |
| 3.63 ± 0.05 | M |
| 2.67 ± 0.02 | M |
| 2.48 ± 0.02 | M | and having the following composition in terms of mole ratios of oxides:

0.9±0.2 $M_{2/n}O:Cr_2O_3:YSiO_2:ZH_2O$, wherein M is at least one cation having a valence of n, Y is a value within the range of about 4 to about 500, and Z is a value within the range of 0 to about 160.

Consequently, according to the present invention, there is provided a process for the conversion of a hydrocarbon stream, which process comprises contacting said stream under hydrocarbon conversion conditions with a crystalline chromosilicate comprising a molecular sieve material providing an X-ray diffraction pattern comprising the following X-ray diffraction lines and assigned strengths:

| Interplanar Spacing d, Å | Assigned Strength |
|---|---|
| 11.15 ± 0.2 | W |
| 9.96 ± 0.2 | VS |
| 5.99 ± 0.1 | VW |
| 5.71 ± 0.1 | VW |
| 4.97 ± 0.1 | W |
| 3.85 ± 0.07 | M |
| 3.82 ± 0.07 | MS |
| 3.75 ± 0.05 | M |
| 3.32 ± 0.05 | VW |
| 1.99 ± 0.02 | W | and having the following composition in terms of mole ratios of oxides:

0.9±0.2 $M_{2/n}O:Cr_2O_3:YSiO_2:ZH_2O$, wherein M is at least one cation having a valence of n, Y is a value within the range of about 4 to about 500, and Z is a value within the range of 0 to about 160.

There is provided also a process for the conversion of a hydrocarbon stream, which process comprises contacting said stream under hydrocarbon conversion conditions with a catalytic composition comprising a mixture of a crystalline chromosilicate and an oxide of chromium, said catalytic composition providing an X-ray diffraction pattern comprising the following X-ray diffraction lines and assigned strengths:

| Interplanar Spacing d, Å | Assigned Strength |
|---|---|
| 11.14 ± 0.2 | M |
| 9.89 ± 0.2 | VS |
| 3.85 ± 0.07 | MS |
| 3.81 ± 0.07 | M |
| 3.72 ± 0.05 | M |
| 3.63 ± 0.05 | M |
| 2.67 ± 0.02 | M |
| 2.48 ± 0.02 | M | and having the following composition in terms of mole ratios of oxides:

0.9±0.2 $M_{2/n}O:Cr_2O_3:YSiO_2:ZH_2O$, wherein M is at least one cation having a valence of n, Y is a value within the range of about 4 to about 500, and Z is a value within the range of 0 to about 160.

Furthermore, according to the present invention, there is provided a process for the isomerization of a xylene feed, which process comprises contacting said feed under isomerization conditions with a crystalline chromosilicate providing an X-ray diffraction pattern comprising the following X-ray diffraction lines and assigned strengths:

| Interplanar Spacing d, Å | Assigned Strength |
|---|---|
| 11.15 ± 0.2 | W |
| 9.96 ± 0.2 | VS |
| 5.99 ± 0.1 | VW |
| 5.71 ± 0.1 | VW |
| 4.97 ± 0.1 | W |
| 3.85 ± 0.07 | M |
| 3.82 ± 0.07 | MS |
| 3.75 ± 0.05 | M |
| 3.32 ± 0.05 | VW |
| 1.99 ± 0.02 | W | and having the following composition in terms of mole ratios of oxides:

0.9±0.2 $M_{2/n}O:Cr_2O_3:YSiO_2:ZH_2O$, wherein M is at least one cation having a valence of n, Y is a value within the range of about 4 to about 500, and Z is a value within the range of 0 to about 160.

There is provided a process for the isomerization of a xylene feed, which process comprises contacting said feed under isomerization conditions with a catalytic composition comprising a mixture of a crystalline chromosilicate and an oxide of chromium, said composition providing an X-ray diffraction pattern comprising the following X-ray diffraction lines and assigned strengths:

| Interplanar Spacing d, Å | Assigned Strength |
|---|---|
| 11.14 ± 0.2 | M |
| 9.89 ± 0.2 | VS |
| 3.85 ± 0.07 | MS |
| 3.81 ± 0.07 | M |
| 3.72 ± 0.05 | M |
| 3.63 ± 0.05 | M |
| 2.67 ± 0.02 | M |
| 2.48 ± 0.02 | M | and having the following composition in terms of mole ratios of oxides:

0.9±0.2 $M_{2/n}O:Cr_2O_3:YSiO_2:ZH_2O$, wherein M is at least one cation having a valence of n, Y is a value within the range of about 4 to about 500, and Z is a value within the range of 0 to about 160.

The AMS-1Cr crystalline chromosilicate can be used as catalysts or as adsorbents either in the alkali metal form (e.g., the sodium form), the ammonium form, the hydrogen form, or any other univalent or multivalent cationic form. Mixtures of cations can be employed. The AMS-1Cr crystalline chromosilicates can also be used in intimate combination with a hydrogenating component such as tungsten, vanadium, molybdenum, rhenium, nickel, cobalt, chromium, manganese, or a noble meal such as platinum or palladium, or rare earth metals, where a hydrogenation-dehydrogenation function is to be performed. Such components can be exchanged into the composition at the cationic sites, represented by the term "M" in the above formulae, impregnated therein, or physically and intimately admixed therewith. In one example, platinum can be placed on the chromosilicate with a platinum-metal-containing ion.

The original cation associated with the AMS-1Cr crystalline chromosilicate can be replaced, as mentioned above, by a wide variety of other cations according to techniques which are known in the art. Ion exchange techniques known in the art are disclosed in many patents including U.S. Pat. Nos. 3,140,249, 3,140,251, and 3,140,253, the teachings of which are incorporated by reference into this specification.

Following ion exchange, impregnation, or contact with another material to place catalytically active materials within or on the chromosilicate structure, the material can be washed and thereafter dried at temperatures in the range of about 150° F. (66° C.) to about 600° F. (316° C.). If the composition contains a mixture of chromosilicate and an oxide of chromium, it can be heated in an oxygen-containing atmosphere at closely regulated temperatures in a range from about 800° F. (427° C.) to about 1,700° F. (927° C.) for various periods of time. If the composition contains a chromosilicate that has been treated previously in a hydrogen-containing atmosphere, the metal-containing chromosilicate should be treated in a hydrogen-containing atmosphere under similar conditions.

For either treatment, a typical time for treatment falls within the range of about 0.2 hr to about 100 hr, preferably, within the range of about 1 hr to about 6 hr. Furthermore, a preferred temperature falls within the range of about 900° F. (482° C.) to about 1,200° F. (649° C.).

Ion exchange at the cationic site within the crystalline material will have a relatively insignificant effect on the overall X-ray diffraction pattern that the crystalline chromosilicate material generates. Small variations may occur at various spacings on the X-ray pattern but the overall pattern remains essentially the same. Small changes in the X-ray diffraction patterns may also be the result of processing differences during manufacture; however, the material will still fall within the generic class of AMS-1Cr crystalline chromosilicate defined in terms of their X-ray diffraction patterns specified herein.

The claimed crystalline chromosilicate may be incorporated as a pure crystalline material in a catalyst or may be admixed with various binders or bases depending upon the specific catalytic processing in which the crystalline chromosilicate is to be used. In many instances, the crystalline chromosilicate can be pelletized or extruded and used as a catalyst or an adsorbent. The crystalline chromosilicate can be combined with active or inactive materials, synthetic or naturally occurring zeolites, as well as inorganic or organic materials which would be useful for holding or binding the crystalline chromosilicate. Well-known materials include silica, silica-alumina, alumina sols, hydrated aluminas, clays such as bentonite or kaolin, or other binders well known in the art. The crystalline chromosilicate content can vary anywhere from a few up to 100 percent of the total finished product.

It is contemplated that catalytically-active metals can be impregnated onto the support, whether the catalytic support is solely a crystalline chromosilicate or a mixture of a chromosilicate and another material, in an amount that falls within the range of about 0.05 wt.% to about 25 wt.%, based upon the weight of the total catalyst. Preferably, such metal or metals can be impregnated to an amount within the range of about 0.2 wt.% to about 16 wt.%, based upon the weight of the catalyst.

In the case of a cation-exchanged metal, the metal can be present in an amount that falls within the range of about 0.01 wt.% to about 10 wt.%, based upon the weight of the sieve material in the catalyst, preferably, within the range of about 0.1 wt.% to about 6 wt.%, based upon the weight of the sieve material.

The AMS-1Cr crystalline chromosilicate can be generally prepared by mixing in an aqueous medium, oxides of chromium in the +3 valence state, sodium or any other alkali metal and silicon, and a tetraalkylammonium compound or an alkylamine. The mole ratios of the various reactants can be varied considerably to produce the AMS-1Cr crystalline chromosilicates. In particular, reactant mole ratios in terms of the various oxides for producing the AMS-1Cr crystalline chromosilicate can vary as is indicated in Table V below.

TABLE V

| Ratio of Reactants | Mole Ratios |
| --- | --- |
| $SiO_2/Cr_2O_3$ | 1–500 |
| $R_4N^+/(R_4N^+ + Na^+)$ | 0.1–1 |
| $OH^-/SiO_2$ | 0.1–10 | wherein R is alkyl, and preferably propyl, and $Na^+$ represents sodium, any other alkali metal, or an alkaline earth metal. The above quantities can be varied in concentration in the aqueous medium. It is generally preferred that the mole ratio of water to the hydroxyl ion vary anywhere from about 10 to about 500, or higher.

Under reasonably controlled conditions the claimed AMS-1Cr crystalline chromosilicate will be produced using the above mole ratios. Typical reaction conditions include heating the reactants to a temperature of anywhere from about 25° C. to about 300° C. for a period of time of anywhere from about a few hours to a few weeks, or more. Preferred temperature ranges are anywhere from about 150° C. to about 180° C. with an amount of time necessary for the precipitation and crystallization of the AMS-1Cr crystalline chromosilicate. Especially preferred conditions include a temperature around 165° C. for a period of about 7 days.

The material thus formed can be separated by well-known means such as filtration and recovered as a crystalline chromosilicate product. This material can be mildly dried for anywhere from a few hours to a few days at varying temperatures to form a dry cake which itself can then be crushed to a powder, or to small particles, and extruded, pelletized, or made into forms suitable for use as a catalyst or as an adsorbent. Typically, the material prepared after the mild drying conditions will contain the tetraalkylammonium ion within the solid mass and a subsequent activation procedure is necessary, if it is desired to remove this material from the formed product.

Generally, the high-temperature treatment conditions will take place at temperatures anywhere from about 800° F. (427° C.) to about 1,600° F. (871° C.), or higher, e.g., 1,700° F. (927° C.). Extreme treatment temperatures may detrimentally alter the crystal structure, or destroy it. There is generally no need for going beyond about 1,200° F. (649° C.) in order to remove the tetraalkylammonium cation from the original crystalline material formed.

The high-temperature treatment is conducted in the presence of a reducing atmosphere of hydrogen. As mentioned above, this treatment should be carried out for a period of time within the range of about 0.2 hr to about 100 hr. A sample of the crystalline chromosilicate having undergone such a high-temperature treatment in a reducing atmosphere of hydrogen will provide an X-ray diffraction pattern, as described herein.

On the other hand, the chromosilicate material can be subjected to a high-temperature treatment in the presence of an oxygen-containing atmosphere, such as air. This treatment then becomes a calcination treatment. The resulting material is found to be a composition comprising a mixture of a crystalline chromosilicate and an oxide of chromium. This composition provides an X-ray diffraction pattern comprising the following X-ray diffraction lines and assigned strengths:

| Interplanar Spacing d, Å | Assigned Strength |
|---|---|
| 11.14 ± 0.2 | M |
| 9.89 ± 0.2 | VS |
| 3.85 ± 0.07 | MS |
| 3.81 ± 0.07 | M |
| 3.72 ± 0.05 | M |
| 3.63 ± 0.05 | M |
| 2.67 ± 0.02 | M |
| 2.48 ± 0.02 | M | and has the following composition in terms of mole ratios of oxides:

$0.9 \pm 0.2\ M_{2/n}O:Cr_2O_3:YSiO_2:ZH_2O$, wherein M is at least one cation having a valence of n, Y is a value within the range of about 4 to about 500, and Z is a value within the range of 0 to about 160.

This composition, a mixture of an oxide of chromium and a crystalline chromosilicate, has been found to be catalytically active for the conversion of hydrocarbons, e.g., the isomerization of a xylene feed.

It appears that the high-temperature treatment of the chromosilicate material in the presence of an oxygen-containing atmosphere operates to remove some chromium from the framework of the molecular sieve material. On the other hand, if the molecular sieve material is subjected to the high-temperature treatment in a reducing atmosphere of hydrogen, no free chromia is detectable in the chromosilicate. The hydrogentreated chromosilicate cation exchanges with mono and divalent cations in the typical manner of conventional aluminosilicates. However, it has been found that if the hydrogen-treated chromosilicate is calcined subsequently in an oxygen-containing atmosphere and then analyzed by X-ray diffraction techniques, the resulting analysis shows that chromia is present in the sample that had been subjected to the oxygen-containing air at the high temperature. It appears that this removal of chromia from the chromosilicate structure is irreversible.

Consequently, there are three compositions which can result from the above-described preparation techniques. Composition A is the chromosilicate material as prepared and only dried at a mild temperature, e.g., 165° C. This composition has the defined X-ray diffraction pattern for the AMS-1Cr crystalline chromosilicate material and does not have any detectable $Cr_2O_3$. Composition A can be converted to either Composition B, or Composition C, depending upon which high-temperature treatment is given to the Composition A. Composition C is made from Composition A, by heat treating the latter in a reducing atmosphere of hydrogen at a high temperature, as described hereinabove. This Composition C provides an X-ray diffraction pattern that is similar to the X-ray diffraction pattern provided by Composition A. On the other hand, Composition B is made by heat treating Composition A or Composition C in an oxygen-containing atmosphere, such as air. It has been found that if the chromium content of the reactant mixture is sufficient, the X-ray diffraction analysis of the molecular sieve-containing product will show some detectable crystalline $Cr_2O_3$ in that sieve product. The $Cr_2O_3$ and the crystalline chromosilicate are present as crystallites of an average diameter of about 500 Å. The dominant chromium oxide is $CrO_3$, when the Si-to-Cr mole ratios are greater than 40. The relationships between Compositions A, B, and C are shown in the accompanying figure.

In view of the above, broadly, there is provided a method for preparing a crystalline chromosilicate, which method comprises: (1) preparing a mixture containing an oxide of silicon, a compound of chromium, a hydroxide of an alkali metal or an alkaline earth metal, an alkylammonium cation or a precursor of an alkylammonium cation, and water; (2) maintaining said mixture at suitable reaction conditions to effect formation of the chromosilicate, said reaction conditions comprising a reaction temperature within the range of about 25° C. to about 300° C., a pressure of at least the vapor pressure of water at the reaction temperature, and a reaction time that is sufficient to effect crystallization to crystals of chromosilicate; and (3) washing and drying said crystals.

Furthermore, there is provided the method which comprises further activating said crystals of chromosilicate as prepared above by heat treating said crystals at a temperature within the range of about 800° F. (427° C.) to about 1,700° F. (927° C.) in the presence of a hydrogen-containing atmosphere.

There is provided, in addition, a method for preparing a catalytic composition, which method comprises: (1) preparing a mixture containing an oxide of silicon, a compound of chromium, a hydroxide of an alkali metal or an alkaline earth metal, an alkylammonium cation or a precursor of an alkylammonium cation, and water; (2) maintaining said mixture at suitable reaction conditions to effect formation of a crystalline material, said reaction conditions comprising a reaction temperature within the range of about 25° C. to about 300° C., a pressure of at least the vapor pressure of water at the reaction temperature, and a reaction time that is sufficient to effect crystallization to crystals of said chromosilicate; (3) washing and drying said crystals; and (4) calcining the resulting product in an oxygen-containing atmosphere at a temperature within the range of about 800° F. (427° C.) to about 1,700° F. (927° C.). Suitable compounds of chromium are $Cr_2(SO_4)_3 \cdot xH_2O$ and $Cr(C_2H_3O_2)_3 \cdot H_2O$.

According to the present invention, there is provided a catalytic composition which comprises a crystalline chromosilicate and a porous refractory inorganic oxide, said chromosilicate and said refractory inorganic oxide having been intimately admixed with one another, said chromosilicate comprising a molecular sieve material providing an X-ray diffraction pattern comprising the following X-ray diffraction lines and assigned strengths:

| Interplanar Spacing d, Å | Assigned Strength |
|---|---|
| 11.15 ± 0.2 | W |
| 9.96 ± 0.2 | VS |
| 5.99 ± 0.1 | VW |
| 5.71 ± 0.1 | VW |
| 4.97 ± 0.1 | W |
| 3.85 ± 0.07 | M |
| 3.82 ± 0.07 | MS |
| 3.75 ± 0.05 | M |
| 3.32 ± 0.05 | VW |
| 1.99 ± 0.02 | W | and having the following composition in terms of mole ratios of oxides:
0.9±0.2 $M_{2/n}O:Cr_2O_3:YSiO_2:ZH_2O$,
wherein M is at least one cation having a valence of n, Y is a value within the range of about 4 to about 500, and Z is a value within the range of 0 to about 160.

Furthermore, there is provided a catalytic composition which comprises a molecular-sieve-containing component and a porous refractory inorganic oxide, said component and said inorganic oxide having been intimately admixed with one another, said component comprising a mixture of a crystalline chromosilicate and an oxide of chromium, providing an X-ray diffraction pattern comprising the following X-ray diffraction lines and assigned strengths:

| Interplanar Spacing d, Å | Assigned Strength |
|---|---|
| 11.14 ± 0.2 | M |
| 9.89 ± 0.2 | VS |
| 3.85 ± 0.07 | MS |
| 3.81 ± 0.07 | M |
| 3.72 ± 0.05 | M |
| 3.63 ± 0.05 | M |
| 2.67 ± 0.02 | M |
| 2.48 ± 0.02 | M | and having the following composition in terms of mole ratios of oxides:
0.9±0.2 $M_{2/n}O:Cr_2O_3:YSiO_2:ZH_2O$,
wherein M is at least one cation having a valence of n, Y is a value within the range of about 4 to about 500, and Z is a value within the range of 0 to about 160.

There is provided a process for the conversion of a hydrocarbon stream, which process comprises contacting said stream under hydrocarbon conversion conditions with a catalytic composition comprising a crystalline chromosilicate and a porous refractory inorganic oxide, said chromosilicate and said refractory inorganic oxide having been intimately admixed with one another, said chromosilicate comprising a molecular sieve material providing an X-ray diffraction pattern comprising the following X-ray diffraction lines and assigned strengths:

| Interplanar Spacing d, Å | Assigned Strength |
|---|---|
| 11.15 ± 0.2 | W |
| 9.96 ± 0.2 | VS |
| 5.99 ± 0.1 | VW |
| 5.71 ± 0.1 | VW |
| 4.97 ± 0.1 | W |
| 3.85 ± 0.07 | M |
| 3.82 ± 0.07 | MS |
| 3.75 ± 0.05 | M |
| 3.32 ± 0.05 | VW |
| 1.99 ± 0.02 | W | and having the following composition in terms of mole ratios of oxides:
0.9±0.2 $M_{2/n}O:Cr_2O_3:YSiO_2:ZH_2O$,
wherein M is at least one cation having a valence of n, Y is a value within the range of about 4 to about 500, and Z is a value within the range of 0 to about 160.

There is provided a process for the isomerization of a xylene feed, which process comprises contacting said feed under isomerization conditions with the catalytic composition comprising a crystalline chromosilicate and a porous refractory inorganic oxide, said chromosilicate and said refractory inorganic oxide having been intimately admixed with one another, said chromosilicate comprising a molecular sieve material providing an X-ray diffraction pattern comprising the following X-ray diffraction lines and assigned strengths:

| Interplanar Spacing d, Å | Assigned Strength |
|---|---|
| 11.15 ± 0.2 | W |
| 9.96 ± 0.2 | VS |
| 5.99 ± 0.1 | VW |
| 5.71 ± 0.1 | VW |
| 4.97 ± 0.1 | W |
| 3.85 ± 0.07 | M |
| 3.82 ± 0.07 | MS |
| 3.75 ± 0.05 | M |
| 3.32 ± 0.05 | VW |
| 1.99 ± 0.02 | W | and having the following composition in terms of mole ratios of oxides:
0.9±0.2$M_{2/n}O:Cr_2O_3:YSiO_2:ZH_2O$,
wherein M is at least one cation having a valence of n, Y is a value within the range of about 4 to about 500, and Z is a value within the range of 0 to about 160.

There is provided a process for the conversion of a hydrocarbon stream, which process comprises contacting said stream under hydrocarbon conversion conditions with a catalytic composition comprising a molecular sieve-containing component and a porous refractory inorganic oxide, said molecular sieve-containing component and said inorganic oxide having been intimately admixed with one another, said molecular sieve-containing component comprising a mixture of a crystalline chromosilicate and an oxide of chromium, providing an X-ray diffraction pattern comprising the following X-ray diffraction lines and assigned strengths:

| Interplanar Spacing d, Å | Assigned Strength |
|---|---|
| 11.14 ± 0.2 | M |
| 9.89 ± 0.2 | VS |
| 3.85 ± 0.07 | MS |

-continued

| Interplanar Spacing d, Å | Assigned Strength |
|---|---|
| 3.81 ± 0.07 | M |
| 3.72 ± 0.05 | M |
| 3.63 ± 0.05 | M |
| 2.67 ± 0.02 | M |
| 2.48 ± 0.02 | M | and having the following composition in terms of mole ratios of oxides:

$0.9 \pm 0.2 \, M_{2/n}O:Cr_2O_3:YSiO_2:ZH_2O$, wherein M is at least one cation having a valence of n, Y is a value within the range of about 4 to about 500, and Z is a value within the range of 0 to about 160.

In addition, there is provided a process for the isomerization of a xylene feed, which process comprises contacting said feed under isomerization conditions with a catalytic composition which comprises a molecular sieve-containing component and a porous refractory inorganic oxide, said molecular sieve-containing component and said inorganic oxide having been intimately admixed with one another, said molecular sieve-containing component comprising a mixture of a crystalline chromosilicate and an oxide of chromium, providing an X-ray diffraction pattern comprising the following X-ray diffraction lines and assigned strengths:

| Interplanar Spacing d, Å | Assigned Strength |
|---|---|
| 11.14 ± 0.2 | M |
| 9.89 ± 0.2 | VS |
| 3.85 ± 0.07 | MS |
| 3.81 ± 0.07 | M |
| 3.72 ± 0.05 | M |
| 3.63 ± 0.05 | M |
| 2.67 ± 0.02 | M |
| 2.48 ± 0.02 | M | and having the following composition in terms of mole ratios of oxides:

$0.9 \pm 0.2 \, M_{2/n}O:Cr_2O_3:YSiO_2:ZH_2O$, wherein M is at least one cation having a valence of n, Y is a value within the range of about 4 to about 500, and Z is a value within the range of 0 to about 160.

There are provided methods for preparing those catalytic compositions which have a molecular sieve-containing component and a porous refractory inorganic oxide intimately admixed with one another. The molecular sieve-containing component can be solely crystalline chromosilicate or it can be a mixture of a crystalline chromosilicate and an oxide of chromium.

There is provided a method for preparing the catalytic composition having a crystalline chromosilicate and a refractory inorganic oxide intimately admixed with one another, which method comprises: (1) preparing a mixture of said chromosilicate in a finely-divided state and a sol, hydrosol, or a hydrogel of said refractory inorganic oxide; (2) thoroughly blending said mixture; (3) adding a gelling medium to the thoroughly-blended mixture to form a gel, if a sol or hydrosol is present; (4) drying said gel; and (5) heat treating said gel in a hydrogen-containing atmosphere at a temperature within the range of about 800° F. (427° C.) to about 1,700° F. (927° C.).

In addition, there is provided a method for preparing a catalytic composition which comprises a molecular sieve-containing component and a porous refractory inorganic oxide, said component and said inorganic oxide having been intimately admixed with one another, said component comprising a mixture of a crystalline chromosilicate and an oxide of chromium, providing an X-ray diffraction pattern comprising the following X-ray diffraction lines and assigned strengths:

| Interplanar Spacing d, Å | Assigned Strength |
|---|---|
| 11.14 ± 0.2 | M |
| 9.89 ± 0.2 | VS |
| 3.85 ± 0.07 | MS |
| 3.81 ± 0.07 | M |
| 3.72 ± 0.05 | M |
| 3.63 ± 0.05 | M |
| 2.67 ± 0.02 | M |
| 2.48 ± 0.02 | M | and having the following composition in terms of mole ratios of oxides:

$0.9 \pm 0.2 \, M_{2/n}O:Cr_2O_3:YSiO_2:ZH_2O$, wherein M is at least one cation having a valence of n, Y is a value within the range of about 4 to about 500, and Z is a value within the range of 0 to about 160, which method comprises: (1) preparing a mixture of said component in a finely-divided state and a sol, a hydrosol, or a hydrogel of a refractory inorganic oxide; (2) thoroughly blending said mixture; (3) adding a gelling medium to the thoroughly-blended mixture to form a gel, if a sol or hydrosol is present; (4) drying said gel; and (5) heat treating said gel in an oxygen-containing atmosphere at a temperature within the range of about 800° F. (427° C.) to about 1,700° F. (927° C.).

In the preparation of either of the above catalytic compositions containing a refractory inorganic oxide, it is contemplated that the molecular sieve-containing component can be cation exchanged prior to its introduction into the sol, hydrosol, or hydrogel of the refractory inorganic oxide. Moreover, it is contemplated that either the molecular sieve-containing component prior to its introduction into the inorganic oxide sol or gel or the finished catalytic composition can be impregnated with a catalytically active metal to form an impregnated material. The impregnated material is then dried and activated by a heat treatment in either an oxygen-containing atmosphere or a hydrogen-containing atmosphere, the selection of which is dependent upon whether the chromosilicate in the composition has seen previously a hydrogen treatment or an oxygen treatment. Conditions for the drying and heat treating are provided hereinabove.

These catalytic compositions which contain a porous refractory inorganic oxide can be used suitably in processes for the conversion of hydrocarbon streams. For example, there is provided a process for the conversion of a hydrocarbon stream, which process comprises contacting said stream under hydrocarbon conditions in the presence of either of these catalytic compositions. Furthermore, there is provided a process for the isomerization of a xylene feed, which process comprises contacting said feed under isomerization conditions in the presence of either of these two catalytic compositions which contain a refractory inorganic oxide.

When the present AMS-1Cr crystalline chromosilicate is used as a hydrocracking catalyst, hydrocracking charge stocks can pass over the catalyst at temperatures anywhere from about 500° F. (260° C.) to about 850° F. (454° C.), or higher, using known molar ratios of hydrocarbon to hydrogen and varying pressures anywhere from a few up to many thousands of pounds per square inch, or higher. The weight hourly space velocity (WHSV) and other process parameters can be varied consistent with the well-known teachings of the art. For example, the pressure can be present within the range of about 20 psig (239 kPa) to about 2,500 psig (17,300 kPa); the WHSV, within the range of about 0.1 weight of hydrocarbon per hour per weight of catalyst ($hr^{-1}$) to about 50 $hr^{-1}$, and the mole ratio of hydrogen to hydrocarbon within the range of about 1 to about 100.

The specified AMS-1Cr crystalline chromosilicate is also suitable as a reforming catalyst to be used with the appropriate hydrogenation components at well-known reforming conditions including temperatures of anywhere from about 500° F. (260° C.) to 1,050° F. (566° C.), or higher, pressures anywhere from a few up to 300 psig (2,170 kPa) to 1,000 psig (6,998 kPa), and weight hourly space velocities and hydrocarbon-to-hydrogen mole ratios consistent with those well known in the reforming art.

The present composition is also eminently suitable for hydrocarbon isomerization and disproportionation. Typically, isomerization can be carried out at a temperature within the range of about 200° F. (93° C.) to about 1,000° F. (538° C.), a hydrogen-to-hydrocarbon mole ratio within the range of about 0 to about 35, a WHSV within the range of about 0.01 $hr^{-1}$ to about 90 $hr^{-1}$, and a pressure within the range of about 0 psig (102 kPa) to about 3,000 psig (20,800 kPa). Advantageously, isomerization can be conducted at a temperature within the range of about 300° F. (149° C.) to about 800° F. (427° C.), a pressure within the range of about 0 psig (102 kPa) to about 3,000 psig (20,800 kPa), a WHSV within the range of about 0.1 $hr^{-1}$ to about 50 $hr^{-1}$, and a hydrogen-to-hydrocarbon mole ratio within the range of 0 to about 35.

It is especially useful for liquid or vapor phase isomerization of xylenes and especially for the isomerization of mixed xylenes to predominantly paraxylene products. Isomerization conditions for the isomerization of xylenes include temperatures of anywhere from about 200° F. (93° C.) to about 1,000° F. (538° C.), hydrogen-to-hydrocarbon mole ratios of from about 0 to about 35, a weight hourly space velocity (WHSV) of about 0.01 weight unit of feed per hour per weight unit of catalyst ($hr^{-1}$) to about 90 $hr^{-1}$, and a pressure of about 0 psig (102 kPa) to about 1,000 psig (6,998 kPa). Advantageously, the conditions comprise a temperature of about 400° F. (204° C.) to about 900° F. (482° C.), a hydrogen-to-hydrocarbon mole ratio of about 0 to about 20, a WHSV of about 1 $hr^{-1}$ to about 20 $hr^{-1}$, and a pressure of about 50 psig (446 kPa) to about 1,000 psig (6,998 kPa). The preferred conditions for the isomerization of xylenes comprise a temperature of about 600° F. (316° C.) to about 850° F. (454° C.), a hydrogen-to-hydrocarbon mole ratio of about 2 to about 8, a WHSV of about 1 $hr^{-1}$ to about 10 $hr^{-1}$, and a pressure of about 100 psig (793 kPa) to about 300 psig (2,170 kPa).

A suitable xylene feed for the isomerization process of the present invention is one that contains less than the thermodynamic-equilibrium concentration of the desired xylene isomers. For example, if one wants to obtain p-xylene, he will employ a feed that contains p-xylene in a concentration that is less than the amount provided by thermodynamic equilibrium.

The choice of catalytically active metals to be placed on the AMS-1Cr crystalline chromosilicate can be selected from any of those well known in the art. Nickel, molybdenum, or a mixture thereof seem to be especially appropriate for isomerization of aromatics. When used as a catalyst in isomerization processes with suitable cations placed on the ion-exchangeable sites within the AMS-1Cr crystalline chromosilicate, reasonably high selectivities for production of desired isomers are obtained.

The claimed AMS-1Cr crystalline chromosilicates can be used as adsorbents to selectively adsorb specific isomers or hydrocarbons in general from a liquid or vapor stream.

The following examples are presented for the purpose of illustration only and are not intended to limit the scope of the present invention. They should not be read to unduly limit or restrict the scope of the appended claims.

EXAMPLE I

The AMS-1Cr crystalline chromosilicate was prepared by dissolving 0.7 gm of $Cr_2(SO_4)_3 \cdot xH_2O$ in 60 gm of distilled water. To this solution was added 2.6 gm of NaOH. The Cr(III) precipitated as the flocculent hydroxide. To the resultant slurry, 10.2 gm of tetra-n-propylammonium bromide (TPABr) were added and the mixture was stirred until the TPABr was dissolved. To this slurry, 13.5 gm of Ludox-AS (30% solids) were added in 4 increments with vigorous stirring. The resulting greenish colloidal solution was placed in a reaction vessel and sealed. The vessel was placed in an oven at 165° C. and left there for 7 days. At the end of this time, the vessel was opened and the contents were removed. The crystalline material was filtered from the mother liquor and was washed with copious quantities of water. The crystalline material was dried in a forced air drying oven at 165° C. and then characterized by X-ray diffraction (XRD). XRD observed 100% crystallinity with the AMS-1Cr pattern for this material reported in Table I above. The yield was approximately 2 gm.

EXAMPLE II

A second preparation of the AMS-1Cr crystalline chromosilicate molecular sieve was performed at slight scale-up and with an alteration of the steps in Example I. A 2.33-gm portion of $Cr_2(SO_4)_3 \cdot xH_2O$ was dissolved in 20 gm of $H_2O$ at 190° F. (88° C.). A 8.7 gm quantity of NaOH was added which resulted in a vigorous evolution of heat. The Cr(III) was apparently in solution as $NaCrO_2$. When 180 gm of $H_2O$ were added to this solution, some Cr(III) did precipitate as the hydroxide. To this slurry were added 31.8 gm of TPABr, which dissolved in the slurry. Finally, 45 gm of Ludox were added in approximately 4 increments in as short a time period as possible. The resulting greenish milky slurry was placed in reaction vessels and then sealed. The vessels were placed in an oven for 7 days at 165° C. After this time period, the vessels were opened and the contents were filtered. The resulting crystalline material was washed with copious quantities of water and then dried in a forced air oven. Again XRD showed 100% crystallinity for the material with the typical AMS-1Cr pattern. The yield of solids was 6.2 gm.

EXAMPLE III

In this example, the AMS-1Cr crystalline chromosilicate of Example I was used.

The crystalline material was calcined at 1,100° F. for 4 hours in air to remove the organic base. The calcined AMS-1Cr material was exchanged with a solution of 20 gm of $NH_4NO_3$ in 200 milliliters of $H_2O$ and a second time with 20 gm of $NH_4(C_2H_3O_2)$ in 200 ml of $H_2O$, both at 190° F. (88° C.) for 2 hours. The exchanged chromosilicate was dried and calcined in air by heating to 900° F. (482° C.) in 4 hours, maintaining the chromosilicate at 900° F. (482° C.) for 4 hours and then cooling to 100° F. (37.8° C.) in 4 hours. The calcined material was exchanged with 100 ml of a 5% Ni($NO_3)_2.6H_2O$ solution for 2 hours at 190° F. (88° C.). The sieve was dried and calcined again using the above calcination procedure.

About 1 gm of the above chromosilicate was dispersed with 6 grams of PHF-$Al_2O_3$ hydrosol (8.7% solids), obtained from the American Cyanamid Company, and mixed thoroughly. One milliliter of distilled water and 1 ml of conc. $NH_4OH$ were mixed and then added to the slurry with intensive mixing. The AMS-1Cr-$Al_2O_3$ gel was placed in the drying oven at 165° C. for 4 hours. The dried solid was again calcined via the above procedure. The calcined catalyst was crushed to 30-50 mesh and activated via a fourth programmed calcination.

The calcined catalyst contained 65 weight percent chromosilicate and 35 weight percent amorphous alumina with approximately 0.5 weight percent of the total catalyst as nickel. This material was analyzed by X-ray diffraction and is reported in Table 1 above.

One gram of the sized and activated catalyst was placed in a microreactor and sulfided with $H_2S$ for 20 minutes at room temperature. The catalyst was then placed under $H_2$ pressure and heated to 600° F. (316° C.). After 1 hour, feed was passed through the microreactor under the following once-through operating conditions:

| | |
|---|---|
| Temperature | 800° F. (427° C.) |
| Pressure | 150 psig (1,136 kPa) |
| WHSV | 5.53 hr$^{-1}$ |
| H/HC mole ratio | 7 |

The liquid feed and liquid effluent streams for this operation are shown below. Because of the equipment limitations on the testing unit, only the liquid streams were specifically reported. The amount of light ends production over this catalyst was determined to be low from the gas chromatographic analysis made on the off-gas stream from the testing unit. The volume of off-gas was, from past performance, determined to not substantially reduce liquid yields of the catalyst.

| Component | Liquid Feed, wt % | Liquid Product, wt % |
|---|---|---|
| Paraffins and naphthenes | .03 | .02 |
| Benzene | — | 3.80 |
| Toluene | .077 | .39 |
| Ethylbenzene | 19.71 | 13.28 |
| Paraxylene | — | 17.54 |
| Metaxylene | 79.80 | 52.27 |
| Orthoxylene | .38 | 10.71 |
| $C_9$, totals | | .29 |
| Methylethylbenzene | | .13 |
| Trimethylbenzene | | .15 |
| Normal propylbenzene | | .01 |
| $C_{10}$, totals | | 1.70 |
| Diethylbenzenes | | 1.32 |
| 1,3 Diethylbenzenes | | .67 |
| 1,4 & 1,2 Diethylbenzenes | | .65 |
| Dimethylethylbenzenes | | .38 |

EXAMPLE IV

In this Example, crystalline chromosilicate prepared in a manner similar to that described in Example I was exposed to high temperature calcination as described in Example II and analyzed to determine its oxide composition. The results are reported below.

| Product Composition, wt % | |
|---|---|
| $SiO_2$ | 80.00 |
| $Cr_2O_3$ | 12.40 |
| $Na_2O$ | 5.39 |
| $Al_2O_3$ | 0.18 |
| $Fe_2O_3$ | 0.11 |
| Volatiles* | 1.92 |
| | 100.00 |
| Mole Ratios | |
| $SiO_2/Cr_2O_3$ | 16.3 |
| $Na_2O/Cr_2O_3$ | 1.1 |
| $SiO_2/Al_2O_3$ | 757.6 |
| $SiO_2/Fe_2O_3$ | 1,960.8 |
| $SiO_2/(Al_2O_3 + Fe_2O_3)$ | 546.4 |

*Assumed value to give 100%.

EXAMPLE V

Another example of AMS-1Cr chromosilicate was prepared. A 4.8-gm portion of $CR_2(SO_4)_3.xH_2O$ was dissolved in 200.0 gm of distilled $H_2O$ at 90° C. Then 5.2 gm of NaOH were added to the stirred solution and dissolved therein. Initially, a gelatinuous solid of chromium hydroxide formed, but as more NaOH dissolved, the amphoteric chromium hydroxide redissolved, presumably as sodium chromite. To the basic solution were added 31.2 gm of tetraethylammonium bromide (TEABr). The TEABr was dissolved in the solution. Finally, 40.6 gm of Ludox AS-30 was added with vigorous stirring. The resulting slurry was divided and transferred to three tubular crystallizers. The slurry was crystallized at 165° C. for 7 days. The solid material was washed with approximately 1 liter of distilled $H_2O$ and then dried at 165° C. for 20 hrs. A sample of the dried material was submitted for XRD analysis and was found to be a crystalline AMS-1Cr. The yield was 13.8 gm. The remaining solid was calcined at 1,000° F. (538° C.) in air for 4 hrs and was also analyzed by XRD. It was found to be a mixture of crystalline AMS-1Cr chromosilicate and $Cr_2O_3$. No attempt was made to quantify the $Cr_2O_3$.

EXAMPLE VI

Another embodiment of a crystalline AMS-1Cr was prepared. First, 3.6 gm of $Cr_2(SO_4)_3.xH_2O$ were dissolved in 200 ml of distilled $H_2O$ at 90° C. To the greenish-blue solution was added 5.4 gm of NaOH. After the initial precipitate dissolved, 31.2 gm of TEABr was added and dissolved. To this final solution, 38.2 gm of Ludox AS-30 was added quickly, and the resultant solution was stirred for approximately 10 minutes. The resulting slurry was divided between three tubular crystallizers and crystallized at 165° C. for 7 days. After crystallization, the solid material was filtered from the crystallization solution and washed with approximately 1 liter of distilled water. The solid material was dried in a forced air oven at 165° C. overnight (approximately 16 hr). XRD analysis of the dried material showed no amorphous band but the peaks had a relatively low set of intensities suggesting the possibility of $SiO_2$. The remainder of the material was calcined in air at 1,000° F. (538° C.) for 4 hours. XRD analysis showed only 50% crystalline AMS-1Cr with $Cr_2O_3$ present.

EXAMPLE VII

For another embodiment of crystalline AMS-1Cr, the following quantities of reactants were used to obtain the initial slurry, as described in Example IV: 2.4 gm of $Cr_2(SO_4)_3.xH_2O$; 200.0 gm of distilled $H_2O$; 2.0 gm of NaOH; 31.5 gm of TPABr; and 38.2 gm of Ludox AS-30. The slurry was crystallized for 7 days at 165° C. The solid material was removed from the crystallizer, washed with approximately 1 liter of distilled $H_2O$, and dried at 165° C. The dried material was then calcined in air at 1,000° F. for 4 hours with a linear heating rate requiring 4 hours to go from 200° F. (93° C.) to 1,000° F. (538° C.). The calcined material was a yellow green instead of the typical $Cr_2O_3$ green for higher chromium concentration factors. XRD analysis indicated a 100% crystalline AMS-1Cr plus $Cr_2O_3$.

EXAMPLE VIII

Additional samples of AMS-1Cr were prepared in a manner similar to that described in the preceding examples. The quantities of reactants used in each of these preparations are presented hereinbelow in Table VII. The amount of chromium that was employed in each preparation is expressed in terms of a "chromium factor". In each case, the crystallization temperature was maintained at 165° C. and the crystallization was carried out for a period of 7 days. After drying, each sample was calcined in air for 4 hr at a temperature of 1,000° F. (538° C.)

with 200 ml of distilled water. The exchange was repeated and the filtered solid was washed with 300 ml of distilled water. The solid material was dried at 165° C. for 2 days and then calcined in air at 900° F. (482° C.) for 4 hr. The calcined material was exchanged with a solution that had been prepared by dissolving 12.8 gm of $Ni(NO_3)_2.6H_2O$ in 250 ml of distilled water at 90° C. for 3 hr. The solid was filtered from the exchange solution and washed with 250 ml of distilled water. The exchanged solid was dried at 165° C. for 3 hr and then calcined at 900° F. (482° C.) overnight. The calcined solid weighed 3.9 gm and was dispersed thoroughly in 25.3 gm of a PHF-$Al_2O_3$ hydrosol (10.7 wt.% $Al_2O_3$) obtained from the American Cyanamid Company. To the dispersed slurry was added a solution of 2 ml of concentrated $NH_4OH$ and 2 ml of distilled $H_2O$ to gel the suspended solid in the alumina. The gel was dried at 165° C. in a forced air oven for 4 hr. The dried solid was then calcined at 900° F. (482° C.) overnight. This catalyst, identified hereinafter as Catalyst No. 2, was prepared to contain 65 wt.% of the nickel-exchanged solid and 35 wt.% of gamma-alumina. Catalyst No. 2 was crushed and sized to a 30-to-50-mesh material, i.e., a material that would pass through a 30-mesh screen (U.S. Sieve Series), but be retained on a 50-mesh screen (U.S. Sieve Series). The sized material was then calcined in air for 4 hr at a temperature of 900° F. (482° C.).

A 1-gm portion of the calcined Catalyst No. 2 was placed in a microreactor and sulfided by passing $H_2S$ over the catalyst at the rate of 0.2 ft$^3$/hr for 20 minutes. The microreactor was pressured with flowing hydrogen to 150 psig (1,138 KPa) and at a flow of 0.3 ft$^3$/hr. The temperature was increased from room temperature to 800° F. (427° C.) in 3 hr. A synthetic reject filtrate of mixed xylenes was passed over the catalyst at a WHSV of approximately 6 hr$^{-1}$, a pressure of 150 psig (1,138 KPa), and a hydrogen rate of 0.3 cu ft per hr. The liquid product was collected and analyzed by gas-chromatographic techniques. The results for the evaluation of this catalyst are shown in Table VIII. This sieve in the catalyst was only 50% crystalline after the initial calci-

TABLE VII
ADDITIONAL CATALYST PREPARATIONS

| Sample No. | 7 | 8 | 9 | 10 | 11 | 12 | 13 |
|---|---|---|---|---|---|---|---|
| Dist. $H_2O$, gm | 180.0 | 1,600.0 | 1,000.0 | 1,000.0 | 200.0 | 200.0 | 200.0 |
| $Cr_2(SO_4)_3.xH_2O$, gm | 2.33 | 28.8 | 24.0 | 24.0 | 7.2 | 9.6 | 14.4 |
| Chromium Factor | X1 | X1.5 | X2 | X3 | X3 | X4 | X6 |
| NaOH, gm | 8.7 | 41.6 | 26.0 | 20.8 | 9.2 | 11.2 | 15.2 |
| TPABr, gm | 31.8 | 249.6 | 156.0 | 156.0 | 31.2 | 31.2 | 31.2 |
| Ludox HS-40, gm | 45.0[1] | 305.6 | 191.0 | 142.2 | 29.0 | 29.0 | 29.0 |
| XRD[2] Results | 50% CRYST. AMS-1Cr | AMS-1Cr + $Cr_2O_3$ | AMS-1Cr + $Cr_2O_3$ | AMS-1Cr + $Cr_2O_3$ | AMS-1Cr + $Cr_2O_3$ | SOME AMS-1Cr, MOSTLY $Cr_2O_3$ | PRIMARILY $Cr_2O_3$ |

[1]Ludox HS-30 was used.
[2]XRD = X-ray Diffraction.

These results show that as the chromium factor became larger, more and more $Cr_2O_3$ was detected in the product.

EXAMPLE IX

Samples Nos. 7, 8, 9, and 10, that were prepared in Example VIII, were used in Catalysts Nos. 2, 3, 4, and 5, respectively.

A 5-gm portion of the Sample No. 7 was ion exchanged with an ammonium acetate solution that had been prepared by dissolving 50 gm of the salt in 500 ml of distilled water at 90° C. for 2 hours. The solid material was filtered from the exchange solution and washed nation and the low xylene isomerization activity for this catalyst is believed to reflect the degree of crystallinity.

A 30-gm portion of Sample No. 8 was ion-exchanged at a temperature of 90° C. for 1 hr with stirring with a solution that had been prepared by dissolving 30 gm of ammonium acetate in 300 ml of distilled water. Similarly, a 60-gm portion of Sample No. 9 was ion-exchanged at a temperature of 90° C. for 1.5 hr with a solution that had been prepared by dissolving 60 gm of ammonium acetate in 300 ml of distilled water. Each exchanged solid was filtered from its exchange solution and washed with 200 ml of distilled water. This exchange for each solid was repeated 4 times. The final exchange was followed with a 300-ml-distilled-water wash. Each solid was then dried at 165° C. for 3 hr and then transferred to the calcining furnace for a program calcination at 900° F. (482° C.) overnight. The program calcination required 3.5 hours to heat from 200° F. (93° C.) to 900° F. (482° C.), 4 hours at 900° F. (482° C.) and a minimum of 3.5 hours to cool to 200° F. (93° C.). Each calcined solid was exchanged with a quantity of 5 wt% solution of $Ni(NO_3)_2.6H_2O$ for 1.5 hr at 90° C., wherein Sample No. 8 used 150 ml of solution and Sample No. 9 used 200 ml of exchange solution. Each exchanged solid was washed with 150 ml of distilled water and filter-dried overnight. The solids were dried at 165° C. for 6 hours and then transferred to the calcining furnace to program calcine in air at 900° F. (482° C.) overnight.

TABLE VIII

| | TEST NO. 2; CATALYST NO. 2 | | | | | |
|---|---|---|---|---|---|---|
| Cut No. | FD[1] | 1 | 2 | 3 | 4 | 5 |
| Temperature, °F. | | 800 | 800 | 920 | 920 | 920 |
| °C. | | 427 | 427 | 493 | 493 | 493 |
| Product Analysis, wt. % | | | | | | |
| Paraffins & Naphthenes | — | — | — | .10 | .16 | .09 |
| Benzene | — | .55 | .11 | .35 | .26 | .30 |
| Toluene | .03 | — | — | .13 | .13 | .14 |
| Ethylbenzene (EB) | 20.97 | 18.94 | 19.91 | 22.4 | 21.74 | 22.4 |
| p-Xylene (pX) | — | 6.30 | 2.96 | 7.37 | 5.43 | 5.88 |
| m-Xylene (mX) | 78.5 | 70.6 | 75.0 | 65.5 | 69.0 | 68.00 |
| o-Xylene (oX) | — | 3.62 | 2.06 | 4.03 | 3.02 | 3.22 |
| $C_9{}^+$ | .5 | — | — | .12 | .25 | — |
| Calculated Results | | | | | | |
| pp $H_2$, psia | | 147.1 | 152.2 | 154.0 | 148.5 | 152.0 |
| H/HC | | 8.4 | 12.1 | 14.5 | 9.1 | 11.9 |
| $t_c$, sec. | | 2.77 | 2.87 | 2.65 | 2.55 | 3.54 |
| WHSV, $hr^{-1}$ | | 5.19 | 3.58 | 3.01 | 4.76 | 3.64 |
| pX PATE, % | | 33.4 | 15.8 | 40.4 | 29.2 | 32.0 |
| mX PATE, % | | 25.0 | 12.2 | 29.3 | 31.0 | 22.8 |
| oX PATE, % | | 16.8 | 8.71 | 18.9 | 13.5 | 14.5 |
| EB Conv., % | | 9.7 | 5.1 | | | |
| Time On Oil, hr | | 16.0 | 40 | 112 | 184 | 217 |

[1]FD = Feed

Each of the solids was dispersed in $PHF\text{-}Al_2O_3$ hydrosol, obtained from the American Cyanamid Company, to make a catalyst composed of 65% nickel-exchanged solid in 35% gamma $Al_2O_3$. The 30 gm of exchanged Sample No. 8 used 185.9 gm of hydrosol and the 60 gm of exchanged Sample No. 9 used 371.4 gm of hydrosol (10.7% solids). Each exchanged material was thoroughly dispersed in hydrosol by mixing for approximately 45 minutes. A solution, consisting of 50 vol% of distilled $H_2O$ and 50 vol% of concentrated $NH_4OH$, was added to gel the slurry. The mixture containing Sample No. 8 used 22 ml of this solution, while the mixture containing Sample No. 9 used 37 ml. Each gelled mass was dried at 165° C. for 3 hr in a forced air drying oven with frequent turning to facilitate drying. The dried material was then program calcined at 900° F. (482° C.) for 4 hr with an additional 4 hr of drying at 200° F. (93° C.) added to the beginning of the program. The calcined material was crushed and sized to obtain a 30-to-50-mesh material, i.e., a material that will pass through a 30-mesh screen (U.S. Sieve Series), but be retained on a 50-mesh screen (U.S. Sieve Series). The catalyst containing Sample No. 8 material is identified hereinafter as Catalyst No. 3, while the catalyst containing Sample No. 9 material is identified hereinafter as Catalyst No. 4.

A 1-gm portion of Catalyst No. 3 was tested for its ability to catalyze the isomerization of a xylene feed, as was done with Catalyst No. 2. The results of this test, Test No. 3, are presented hereinafter in Table IX. In a like manner, a 1-gm portion of Catalyst No. 4 was tested in a test, identified hereinafter as Test No. 4. The results of Test No. 4 are presented hereinafter in Table X. The tests were conducted at a pressure of 150 psig (1,138 KPa) and a hydrogen flow rate of 0.3 cu ft per hr. The time on oil is expressed as the total time to the end of the particular cut.

A portion of Sample No. 10 was prepared into a catalyst and tested for xylene isomerization in a manner similar to that used hereinabove for Catalyst No. 2 and Catalyst No. 3. This catalyst is identified hereinafter as Catalyst No. 5 and its test, as Test No. 5. The results of Test No. 5 are shown in Table XI.

The relative comparisons of PATEs for the three xylene isomers indicate that this catalyst prepared from a Composition B material exhibits shape selectivity for xylene isomerization. The basic indication for shape selectivity is the high PATE values for ortho-xylene and para-xylene when compared to meta-xylene. This particular evaluation has been indicated by tests run on the AMS-1 family sieves using an 80% m-xylene/20% ethylbenzene feed. The material designated Composition B does not consistently show the shape selective characteristic. This catalyst is the only material other than the material of Examples I and III to demonstrate shape selectivity.

EXAMPLE X

This example describes the procedure used to detect the presence of $Cr_2O_3$ in the air-calcined material herein described as Composition B. The X-ray diffraction procedure for determining free $Cr_2O_3$ in a AMS-type molecular sieve is based on the ratio of the integrated intensities of the sum of the 2.67 Å and 2.65 Å peaks, divided by the intensity of the 2.73 Å peak. Physical blends of sieve and $Cr_2O_3$ over the concentration range desired serve as calibration standards. The peak at 2.56 Å is the strongest XRD peak characteristic of $Cr_2O_3$. It is frequently not well-resolved from the 2.65 Å sieve peak; hence, the use of a sum. The 2.73 Å peak is a convenient, well-resolved sieve peak which acts as an internal standard to make the measurements independent of many experimental variables. Copper K radiation monochromatized by a graphite crystal was used for all experiments. Samples were slow scanned at 0.125° two-theta per minute and peak areas were measured by planimetry.

TABLE IX

| | TEST RESULTS - TEST NO. 3 CATALYST NO. 3 | | | | | | | | | | | |
|---|---|---|---|---|---|---|---|---|---|---|---|---|
| Cut No. | FD[1] | 1 | 2 | 3 | 4 | 5 | 6 | 7 | 8 | 9 | 10 | 11 | 12 |
| Temperature, °F. | | 800 | 800 | 840 | 800 | 840 | 800 | 800 | 800 | 840 | 840 | 880 | 880 |
| °C. | | 427 | 427 | 449 | 427 | 449 | 427 | 427 | 427 | 449 | 449 | 471 | 471 |
| Product Analysis, wt. % | | | | | | | | | | | | | |
| Paraffins & Naphthenes | .05 | .01 | .02 | .02 | .02 | .02 | .02 | .03 | .05 | .05 | .01 | .03 | .08 |
| Benzene | — | .67 | .60 | .90 | .66 | 1.00 | .57 | .33 | .42 | .51 | .62 | 1.00 | 1.95 |

TABLE IX-continued

TEST RESULTS - TEST NO. 3
CATALYST NO. 3

| Cut No. | FD[1] | 1 | 2 | 3 | 4 | 5 | 6 | 7 | 8 | 9 | 10 | 11 | 12 |
|---|---|---|---|---|---|---|---|---|---|---|---|---|---|
| Toluene | .07 | .15 | .14 | .18 | .15 | .20 | .13 | .11 | .12 | .12 | .14 | .21 | .29 |
| Ethylbenzene (EB) | 19.56 | 17.96 | 17.98 | 17.54 | 18.01 | 17.42 | 18.12 | 18.50 | 18.29 | 18.15 | 17.97 | 17.24 | 16.48 |
| p-Xylene (pX) | 8.65 | 17.21 | 16.92 | 17.96 | 17.17 | 18.23 | 16.72 | 14.50 | 15.98 | 16.05 | 16.90 | 18.12 | 18.47 |
| m-Xylene (mX) | 47.83 | 42.06 | 42.17 | 41.55 | 41.98 | 41.36 | 42.11 | 43.50 | 42.53 | 42.58 | 41.98 | 41.34 | 42.91 |
| o-Xylene (oX) | 23.66 | 21.37 | 21.53 | 21.05 | 21.44 | 20.89 | 21.75 | 22.70 | 22.00 | 22.12 | 21.85 | 21.20 | 19.84 |
| $C_9^+$ | .22 | .57 | .64 | .82 | .57 | .88 | .58 | .33 | .61 | .44 | .53 | .86 | — |
| Diethylbenzene | — | .31 | .35 | .40 | .28 | .42 | .31 | .13 | .26 | .20 | .25 | .38 | — |
| Calculated Results | | | | | | | | | | | | | |
| $ppH_2$, psia | | 140.6 | 140.2 | 141.0 | 141.4 | 145.9 | 145.3 | 102.1 | 147.4 | 139.3 | 138.5 | 139.6 | — |
| H/HC | | 5.8 | 5.7 | 6.0 | 6.1 | 7.8 | 7.5 | 3.1 | 8.5 | 5.5 | 5.3 | 5.6 | — |
| $t_c$, sec. | | 2.65 | 2.64 | 2.57 | 2.66 | 2.66 | 2.74 | 1.92 | 2.78 | 2.54 | 2.53 | 2.47 | — |
| WHSV, $hr^{-1}$ | | 6.57 | 6.68 | 6.43 | 6.31 | 4.93 | 5.12 | 12.23 | 4.49 | 6.97 | 7.24 | 6.88 | — |
| pX PATE, % | | 83.4 | 80.6 | 91.5 | 83.1 | 94.3 | 78.7 | 56.7 | 71.6 | 72.2 | 80.6 | 93.4 | 95.6 |
| mX PATE, % | | 99.6 | 97.7 | 104.5 | 100.5 | 106.8 | 98.3 | 76.5 | 90.8 | 89.6 | 99.0 | 105.9 | 86.1 |
| oX PATE, % | | 59.2 | 55.2 | 70.5 | 57.2 | 74.1 | 49.6 | 27.3 | 43.1 | 44.2 | 51.0 | 71.4 | 112.3 |
| EB Conv., % | | 8.2 | 8.1 | 10.3 | 7.9 | 10.9 | 7.4 | 5.4 | 6.5 | 7.2 | 8.1 | 11.9 | 15.7 |
| Time On Oil, hr | | 16.5 | 24.0 | 41.25 | 48.0 | 64.5 | 72.25 | 88.0 | 95.6 | 112.0 | 119.0 | 136.0 | 143.0 |

[1]FD = Feed

TABLE X

TEST RESULTS - TEST NO. 4
CATALYST NO. 4

| Cut No. | FD[1] | 1 | 2 | 3 | 4 | 5 | 9 | 10 | 11 |
|---|---|---|---|---|---|---|---|---|---|
| Temperature, °F. | | 800 | 800 | 840 | 800 | 840 | 840 | 840 | 880 |
| Temperature, °C. | | 427 | 427 | 449 | 427 | 449 | 449 | 449 | 471 |
| Product Analysis, wt. % | | | | | | | | | |
| Paraffins & Naphthenes | .05 | .04 | .03 | .02 | .03 | .03 | .06 | .04 | .02 |
| Benzene | — | .88 | .80 | 1.20 | .92 | 1.65 | 1.13 | 1.16 | 1.13 |
| Toluene | .07 | .16 | .15 | .20 | .17 | .25 | .17 | .19 | .22 |
| Ethylbenzene (EB) | 19.56 | 17.53 | 17.71 | 17.02 | 17.47 | 16.37 | 17.19 | 17.12 | 17.21 |
| p-Xylene (pX) | 8.65 | 17.30 | 16.91 | 17.93 | 17.16 | 18.49 | 17.65 | 17.85 | 18.17 |
| m-Xylene (mX) | 47.83 | 42.18 | 42.35 | 41.78 | 42.07 | 41.42 | 41.84 | 41.69 | 41.27 |
| o-Xylene (oX) | 23.66 | 21.19 | 21.45 | 20.97 | 21.30 | 20.62 | 21.22 | 21.14 | 21.15 |
| $C_9^+$ | .22 | .62 | .62 | .88 | .88 | 1.17 | .74 | .81 | .83 |
| Diethylbenzene | — | .43 | .37 | .48 | .51 | .61 | .38 | .42 | .36 |
| Calculated Results | | | | | | | | | |
| $ppH_2$, psia | | 144.0 | 131.6 | 134.5 | 135.1 | 142.0 | 140.0 | 134.6 | 138.0 |
| H/HC | | 6.9 | 4.8 | 4.4 | 4.6 | 6.2 | 5.7 | 4.5 | 5.2 |
| $t_c$, sec. | | 2.71 | 2.48 | 2.46 | 2.55 | 2.59 | 2.56 | 2.46 | 2.44 |
| WHSV, $hr^{-1}$ | | 5.51 | 9.61 | 8.61 | 8.39 | 6.13 | 6.76 | 8.57 | 7.40 |
| pX PATE, % | | 84.2 | 80.4 | 90.9 | 83.1 | 96.8 | 88.1 | 90.1 | 94.0 |
| mX PATE, % | | 97.9 | 95.3 | 101.8 | 98.5 | 106.3 | 101.1 | 103.2 | 106.5 |
| oX PATE, % | | 63.8 | 58.11 | 73.4 | 60.2 | 81.4 | 67.1 | 69.0 | 72.3 |
| EB Conv., % | | 10.4 | 9.5 | 13.0 | 10.7 | 16.3 | 12.1 | 12.5 | 12.0 |
| Time On Oil, hr | | 16.6 | 24.1 | 41.35 | 48.1 | 113.1 | 160.6 | 167.6 | 184.6 |

[1]FD = Feed

TABLE XI

TEST RESULTS - TEST NO. 5
CATALYST NO. 5

| Cut No. | FD[1] | 1 | 2 | 3 | 4 | 5 | 6 | 7 | 8 | 9 |
|---|---|---|---|---|---|---|---|---|---|---|
| Temperature, °F. | | 800 | 800 | 840 | 840 | 840 | 880 | 878 | 882 | 880 |
| Temperature, °C. | | 427 | 427 | 449 | 449 | 449 | 471 | 470 | 472 | 471 |
| Product Analysis, wt. % | | | | | | | | | | |
| Paraffins & Naphthenes | .05 | | .05 | .07 | .02 | .05 | — | .05 | — | — |
| Benzene | — | .76 | .67 | 1.07 | 1.10 | 1.67 | 1.93 | 1.97 | 2.00 | 2.04 |
| Toluene | .07 | .13 | .11 | .23 | .16 | .24 | .27 | .27 | .28 | .26 |
| Ethylbenzene (EB) | 19.56 | 18.29 | 18.39 | 17.40 | 17.39 | 16.53 | 16.68 | 16.52 | 16.36 | 16.18 |
| p-Xylene (pX) | 8.65 | 15.63 | 15.16 | 17.02 | 17.33 | 18.08 | 18.33 | 18.56 | 18.16 | 18.68 |
| m-Xylene (mX) | 47.83 | 44.41 | 44.64 | 42.74 | 42.69 | 42.20 | 42.89 | 42.91 | 43.16 | 42.95 |
| o-Xylene (oX) | 23.66 | 20.79 | 20.98 | 20.64 | 20.59 | 20.29 | 19.89 | 19.72 | 20.04 | 19.90 |
| $C_9^+$ | .22 | — | — | — | .72 | .94 | — | — | — | — |
| Diethylbenzene | — | — | — | — | .39 | .46 | — | — | — | — |
| Calculated Results | | | | | | | | | | |
| $ppH_2$, psia | | 144.5 | 136.7 | 141.3 | 146.5 | 141.6 | 142.1 | 145.3 | 142.9 | 148.9 |
| H/HC | | 7.1 | 4.9 | 6.0 | 8.1 | 6.1 | 6.3 | 7.5 | 6.6 | 9.4 |
| $t_c$, sec. | | 2.72 | 2.58 | 2.58 | 2.68 | 2.58 | 2.52 | 2.58 | 2.53 | 2.64 |
| WHSV, $hr^{-1}$ | | 5.36 | 7.84 | 6.34 | 4.74 | 6.26 | 6.10 | 5.11 | 5.83 | 4.06 |
| pX PATE, % | | 67.6 | 63.0 | 82.5 | 85.1 | 92.6 | 94.4 | 96.5 | 92.2 | 97.0 |
| mX PATE, % | | 62.8 | 58.6 | 84.1 | 86.7 | 94.1 | 85.5 | 85.9 | 83.3 | 88.0 |
| oX PATE, % | | 74.5 | 69.6 | 80.0 | 82.7 | 90.2 | 110.2 | 115.0 | 106.2 | 112.7 |
| EB Conv., % | | 6.49 | 6.0 | 11.0 | 11.1 | 15.5 | 14.7 | 15.5 | 16.4 | 17.3 |

TABLE XI-continued

| | | TEST RESULTS - TEST NO. 5 CATALYST NO. 5 | | | | | | | |
|---|---|---|---|---|---|---|---|---|---|
| Cut No. | FD[1] | 1 | 2 | 3 | 4 | 5 | 6 | 7 | 8 | 9 |
| Temperature, °F. | | 800 | 800 | 840 | 840 | 840 | 880 | 878 | 882 | 880 |
| Temperature, °C. | | 427 | 427 | 449 | 449 | 449 | 471 | 470 | 472 | 471 |
| Time On Oil, hr | | 17.0 | 24.0 | 41.0 | 45.0 | 65.0 | 72.0 | 89.0 | 106.0 | 114.0 |

[1]FD = Feed

EXAMPLE XI

The air-calcined material was shown by X-ray diffraction analysis to be a mixture of crystalline chromosilicate and $Cr_2O_3$, which mixture has been shown to have catalytic activity to selectively isomerize mixed xylenes to a thermodynamic equilibrium mixture of mixed xylenes enriched in para-xylene concentration. On a theoretical basis, one could argue that this mixture of oxides could be made by impregnating an AMS-1-type silica sieve with suitable chromia salts, which after calcination would yield an elemental oxide mixture that would have the characteristics of the above mixture.

A chromium acetate solution was prepared by dissolving 11.7 gm of chromium acetate in 17.0 gm of distilled $H_2O$ and 3.0 gm of acetic acid. After the solution was prepared, 3.8 gm of AMS-1 silica sieve, having an XRD pattern of the AMS-1 family, were uniformly impregnated with 2.3 gm of the above solution and 1.0 gm of additional water was added to the mixture to attain the water pore volume of the sieve. The impregnated material was allowed to equilibrate for 1 hr and was then slowly dried to attain a uniform impregnation of chromium on the sieve. The partially dried material was given further drying at 165° C. overnight in a Thelco forced air drying oven. The dried and impregnated sieve was calcined for 4 hr at 1,000° F. (538° C.) using the programmed calcination as previously described. The impregnated sieve (3.7 gm) was dispersed in 22.9 gm of PHF-alumina hydrosol (10.7 wt.% solids). A 15-gm quantity of distilled $H_2O$ was added to the slurry. The total slurry was heated to 190° F. (88° C.) and stirred for 1.5 hr. An 8-ml portion of a solution prepared from 4 ml of distilled $H_2O$ and 4 ml of concentrated ammonium hydroxide was added to the slurry to gel the slurry. The slurry was dried at 165° C. overnight in the forced draft drying oven. The dried material was calcined at 1,000° F. (538° C.) for 4 hr using the calcination program as previously described. The calcined material was crushed and sieved for 30 to 50 mesh and then program-calcined at 1,000° F. (538° C.) for 4 hr again. A 1-gm sample of the catalyst, identified hereinafter as Catalyst No. 6, was tested for xylene isomerization in the same manner as described in Test No. 2. This test, identified hereinafter as Test No. 6, furnished results, which are shown in Table XII. From these results, it can be seen that the impregnation of $Cr_2O_3$ on the AMS-1 silica sieve yields a catalyst which has no useful xylene isomerization activity.

EXAMPLE XII

A sample of Catalyst No. 5 was given another treatment in air but at 900° F. (482° C.) for 4 hr to maximize the migration of chromia in the catalyst. This recalcined catalyst, identified hereinafter as Catalyst No. 7, was tested in the same manner as the catalyst in Test No. 2 was tested. The results are shown in Table XIII and are the same as the results for the catalyst of Test No. 6. Therefore, it can be concluded that the catalyst prepared from the impregnation of $Cr_2O_3$ in AMS-1 silica sieve does not reproduce the xylene isomerization activity of the air-calcined material, as shown in Test No. 2.

TABLE XII

| | | TEST RESULTS - TEST NO. 6 CATALYST NO. 6 | | | | | | | | |
|---|---|---|---|---|---|---|---|---|---|---|
| Cut No. | FD[1] | 2 | 3 | 4 | 5 | 6 | 7 | 8 | 9 | 10 |
| Temperature, °F. | | 600 | 640 | 680 | 720 | 760 | 800 | 840 | 840 | 880 |
| Temperature, °C. | | 316 | 338 | 360 | 382 | 404 | 427 | 449 | 449 | 471 |
| Product Analysis, wt. % | | | | | | | | | | |
| Paraffins & Naphthenes | — | — | — | — | — | — | — | — | — | — |
| Benzene | — | — | — | — | — | — | — | — | — | — |
| Toluene | .06 | .07 | — | .07 | .06 | .06 | .07 | .09 | .07 | .11 |
| Ethylbenzene (EB) | 19.12 | 19.06 | 19.10 | 19.06 | 19.10 | 19.09 | 18.82 | 18.98 | 19.07 | 19.09 |
| p-Xylene (pX) | 9.05 | 9.09 | 9.05 | 9.02 | 9.10 | 9.08 | 9.15 | 9.12 | 9.22 | 9.28 |
| m-Xylene (mX) | 48.25 | 48.20 | 48.28 | 48.24 | 48.22 | 48.25 | 48.14 | 48.20 | 48.13 | 48.05 |
| o-Xylene (oX) | 23.52 | 23.58 | 23.58 | 23.61 | 23.52 | 23.53 | 23.81 | 23.62 | 23.51 | 23.43 |
| $C_9^+$ | — | — | — | — | — | — | — | — | — | — |
| Diethylbenzene | — | — | — | — | — | — | — | — | — | — |

[1]FD = Feed

TABLE XIII

| | TEST RESULTS - TEST NO. 7 CATALYST NO. 7 | | |
|---|---|---|---|
| Cut No. | FD[1] | 1 | 2 |
| Temperature, °F. | | 600 | 720 |
| Temperature, °C. | | 316 | 382 |
| Product Analysis, wt. % | | | |
| Paraffins & Naphthenes | — | — | — |
| Benzene | — | — | — |
| Toluene | .06 | — | .08 |
| Ethylbenzene (EB) | 19.12 | 19.16 | 19.13 |
| p-Xylene (pX) | 9.05 | 9.14 | 9.05 |
| m-Xylene (mX) | 48.25 | 48.20 | 48.25 |
| o-Xylene (oX) | 23.52 | 23.50 | 23.49 |
| $C_9^+$ | — | — | — |
| Diethylbenzene | — | — | — |
| Cut No. | 3 | 4 | 5 |
| Temperature, °F. | 720 | 720 | 800 |
| Temperature, °C. | 382 | 382 | 427 |
| Product Analysis, wt. % | | | |
| Paraffins & Naphthenes | — | — | — |
| Benzene | — | — | — |

TABLE XIII-continued

TEST RESULTS - TEST NO. 7
CATALYST NO. 7

| | | | |
|---|---|---|---|
| Toluene | .05 | .07 | .06 |
| Ethylbenzene (EB) | 19.11 | 19.09 | 19.12 |
| p-Xylene (pX) | 9.04 | 9.04 | 9.08 |
| m-Xylene (mX) | 48.27 | 48.27 | 48.25 |
| o-Xylene (oX) | 23.52 | 23.53 | 23.49 |
| $C_9^+$ | — | — | — |
| Diethylbenzene | — | — | — |

[1]FD = Feed

EXAMPLE XIII

This example is provided to show that the results obtained from the use of an air-calcined chromosilicate, such as Sample No. 7, to isomerize a xylene feed cannot be reproduced by use of a material that is prepared by the impregnation of a silica gel with $Cr_2O_3$.

Grade 59 silica gel, obtained from the Davison Chemical Division of W. R. Grace & Company, was crushed and sieved to provide a 30-to-50-mesh material. A 15.2-gm portion of this sieved material was uniformly impregnated with 9.2 gm of the chromium acetate solution that had been prepared in Example XI and 10.0 gm of distilled $H_2O$ were added to achieve a pore-volume filling of solution. The impregnated material was allowed to equilibrate for 1.5 hr and then carefully dried in a forced-draft oven at 165° C. with further drying at 165° C. overnight. The dried and impregnated silica was given a programmed calcination at 1,000° F. (538° C.) for 4 hr, as described hereinbefore. (This impregnated material was calcined with the Catalyst No. 6 during the second programmed calcination of Example XI.) One gram of this chromia-on-Grade 59 silica was tested for xylene isomerization in the same manner as used in Example IX. This chromia-on-Grade 59 silica gel is identified hereinafter as Catalyst No. 8 and the test as Test No. 8, the results of which are presented in Table XIV. This catalyst was found to be inactive for xylene isomerization.

EXAMPLE XIV

Using the same technique that was employed in Example X, 5 gm of Catalyst No. 6 were given another programmed calcination, but at a temperature of 900° F. (482° C.), to maximize any migration of the chromia. The resultant material is identified hereinafter as Catalyst No. 9.

A 1-gm portion of Catalyst No. 9 was tested for xylene isomerization in Test No. 9 in the same manner that was employed in Example IX. The results of this Test No. 9 are presented in Table XV and show that Catalyst No. 9 was relatively inert for xylene isomerization.

As shown in the previous examples, the crystalline chromosilicate material that is prepared by crystallization and subsequent drying at a mild temperature, e.g., 165° C., does provide the X-ray diffraction pattern specified hereinabove. This material has been designated as Composition A. Upon calcination of Composition A in air at a temperature of about 1,000° F. (538° C.) for a period of time of about 4 hr, Composition B forms. Composition B has been shown to be a mixture of an oxide of chromium, i.e., $Cr_2O_3$, and a molecular sieve material, presumably a chromosilicate sieve. This mixture provides an X-ray diffraction pattern that is similar to that provided by Composition A. Upon increasing the amount of chromium in the crystallization mixture of reactants, as demonstrated hereinbefore by larger chromium factors, various peaks in the X-ray diffraction pattern that correspond to those produced by chromia are enlarged. This Composition B, when prepared into a catalyst, has shown activity for the conversion of hydrocarbons, e.g., the isomerization of xylenes. It has been found that such catalytic activity of Composition B cannot be duplicated by impregnation of an AMS-1-type silica sieve with chromia, $Cr_2O_3$. Furthermore, the silica of Composition B is not the same as the silica of the AMS-1-type molecular sieve.

TABLE XIV

TEST RESULTS - TEST No. 8
CATALYST NO. 8

| Cut No. | FD[1] | 1 | 2 | 3 |
|---|---|---|---|---|
| Temperature, °F. | | 600 | 600 | 640 |
| Temperature, °C. | | 316 | 316 | 338 |
| *Product Analysis, wt. %* | | | | |
| Paraffins & Naphthenes | — | — | — | — |
| Benzene | — | .18 | — | — |
| Toluene | .06 | .10 | .08 | .05 |
| Ethylbenzene (EB) | 19.12 | 18.70 | 19.05 | 19.12 |
| p-Xylene (pX) | 9.05 | 10.16 | 9.06 | 9.06 |
| m-Xylene (mX) | 48.25 | 47.60 | 48.29 | 48.22 |
| o-Xylene (oX) | 23.52 | 23.25 | 23.52 | 23.56 |
| $C_9^+$ | — | — | — | — |
| Diethylbenzene | — | — | — | — |

| Cut No. | 4 | 5 | 6 | 7 |
|---|---|---|---|---|
| Temperature, °F. | 680 | 720 | 760 | 800 |
| Temperature, °C. | 360 | 382 | 404 | 427 |
| *Product Analysis, wt. %* | | | | |
| Paraffins & Naphthenes | — | — | — | — |
| Benzene | — | — | — | — |
| Toluene | .07 | .07 | .06 | .09 |
| Ethylbenzene (EB) | 19.04 | 19.18 | 19.11 | 19.06 |
| p-Xylene (pX) | 9.00 | 9.10 | 9.02 | 9.04 |
| m-Xylene (mX) | 48.29 | 48.15 | 48.26 | 48.29 |
| o-Xylene (oX) | 23.60 | 23.56 | 23.54 | 23.51 |
| $C_9^+$ | — | — | — | — |
| Diethylbenzene | — | — | — | — |

| Cut No. | 8 | 9 | 10 |
|---|---|---|---|
| Temperature, °F. | 840 | 840 | 880 |
| Temperature, °C. | 449 | 449 | 471 |
| *Product Analysis, wt. %* | | | |
| Paraffins & Naphthenes | — | — | — |
| Benzene | — | — | — |
| Toluene | .07 | .08 | .09 |
| Ethylbenzene (EB) | 18.90 | 19.12 | 19.06 |
| p-Xylene (pX) | 9.03 | 9.07 | 9.02 |
| m-Xylene (mX) | 48.14 | 48.26 | 48.27 |
| o-Xylene (oX) | 23.86 | 23.48 | 23.57 |
| $C_9^+$ | — | — | — |
| Diethybenzene | — | — | — |

[1]FD = Feed

TABLE XV

TEST RESULTS - TEST NO. 9
CATALYST NO. 9

| Cut No. | FD[1] | 1 | 2 |
|---|---|---|---|
| Temperature, °F. | | 600 | 720 |
| Temperature, °C. | | 316 | 382 |
| *Product Analysis, wt. %* | | | |
| Paraffins & Naphthenes | — | — | — |
| Benzene | — | — | — |
| Toluene | .06 | .08 | .07 |
| Ethylbenzene (EB) | 19.12 | 19.14 | 19.09 |
| p-Xylene (pX) | 9.05 | 9.07 | 9.01 |
| m-Xylene (mX) | 48.25 | 48.15 | 48.24 |
| o-Xylene (oX) | 23.52 | 23.52 | 23.55 |
| $C_9^+$ | — | — | — |
| Diethylbenzene | — | — | — |

| Cut No. | 3 | 4 | 5 |
|---|---|---|---|
| Temperature, °F. | 720 | 720 | 800 |

TABLE XV-continued
TEST RESULTS - TEST NO. 9
CATALYST NO. 9

| Temperature, °C. | 382 | 382 | 427 |
|---|---|---|---|
| Product Analysis, wt. % | | | |
| Paraffins & Naphthenes | — | — | — |
| Benzene | — | — | — |
| Toluene | .08 | .06 | .05 |
| Ethylbenzene (EB) | 19.11 | 19.10 | 19.06 |
| p-Xylene (pX) | 9.02 | 9.03 | 9.12 |
| m-Xylene (mX) | 48.23 | 48.25 | 48.18 |
| o-Xylene (oX) | 23.57 | 23.56 | 23.60 |
| $C_9{}^+$ | — | — | — |
| Diethylbenzene | — | — | — |

[1]FD = Feed

EXAMPLE XV

In this example, a crystalline chromosilicate was prepared, during the preparation of which a treatment in hydrogen was employed.

First, 9.6 gm of $Cr_2(SO_4)_3 \cdot xH_2O$ were dissolved in 400 gm of distilled $H_2O$. To this solution were added 5.2 gm of NaOH. After the NaOH was dissolved in the solution, 62.4 gm of tetra-n-propylammonium bromide (TPABr) were added to that solution and dissolved therein. Then 76.4 gm of Ludox HS-40 were added to the solution with vigorous stirring. A slurry resulted and was placed into a crystallization vessel and crystallized at a temperature of 165° C. for 7 days. The contents were then removed from the crystallizer and the solid material was filtered from the solution and was washed with at least twice the volume of $H_2O$ that had been used in the original crystallization solution. The solid was subsequently filter dried and then placed in a forced-air drying oven for drying overnight at a temperature of about 165° C.

The dried solid was charged to a stainless steel tube reactor which was fixed in a vertical position in a Lundberg 3-Zone furnace. Air was purged from the system overnight with a flow of helium of approximately 1.5 standard cubic feet per hour (SCFH) while the Eurotherm furnace controls were set at a temperature of 200° F. (93° C.). The helium flow was stopped and a flow of hydrogen of about 3 SCFH was initiated. The temperature setting for the furnace was increased 50° F. every 15 minutes until a temperature of 1,000° F. (538° C.) was attained. The temperature was then held at 1,000° F. (538° C.) for 4 hr, after which the temperature controls were set at 200° F. (93° C.) and the furnace, the reactor, and the contents of the reactor were allowed to cool to 200° F. (93° C.) overnight. When the temperature settings were changed to 200° F. (93° C.), the hydrogen flow was stopped and a flow of helium of about 1.5 SCFH was started, in order to purge the hydrogen from the system overnight. The solid material was cooled, purged with helium, and removed from the tube furnace. This solid material was analyzed by X-ray diffraction and found to be AMS-1Cr crystalline chromosilicate. No free $Cr_2O_3$ was found to be present. This material, identified as Sample No. 14, is hydrogen-treated crystalline chromosilicate and represents an embodiment of Composition C, which has been discussed hereinabove.

Approximately 1 gm of Sample No. 14 was calcined in air at a temperature of 1,000° F. (538° C.) for 4 hr. X-ray diffraction analysis of this calcined material showed that it comprised crystalline chromosilicate and approximately 10 wt.% $Cr_2O_3$.

EXAMPLE XVI

This example is presented to demonstrate that the AMS-1Cr crystalline chromosilicate that has been hydrogen treated at a high temperature can be cation-exchanged with calcium ions.

A 5-gm portion of Sample No. 14 obtained from Example XV was cation-exchanged 5 times with calcium acetate solutions. Each solution had been prepared by dissolving 10 gm of calcium acetate in 150 ml of distilled $H_2O$. In addition, the second exchange was performed with the exchange solution after its initial pH had been adjusted to a value of 3.0 by the addition of dilute nitric acid. Each exchange was carried out for a period of 1.5 hr at a temperature of 190° F. (88° C.). The original Sample No. 14 contained 5.20 wt.% chromium and 0.55 wt.% sodium, on an ignited basis. The exchanged material contained, on an ignited basis, 3.68 wt.% chromium, 1.45 wt.% calcium, and 0.051 wt.% sodium. On the basis of 100 gm, the exchanged AMS-1Cr chromosilicate would contain 3.68/52.01 moles of chromium, i.e., 0.708 moles of chromium; (1.45)(2)/40.08 equivalents of calcium, i.e., 0.0723 equivalents of calcium; and 0.051/22.997 equivalents of sodium, i.e., 0.0021 equivalents of sodium. Hence, there are 0.0744 equivalents of exchangeable cation. Consequently, the equivalents of exchangeable cation are within 5% of being equal to the moles of tetrahedral chromium. This furnishes a necessary prerequisite for the chromium to be considered within the framework of the molecular sieve material. The acid treatment of the second exchange leached out some chromium from the sieve framework.

EXAMPLE XVII

In this example, a catalyst containing a nickel-exchanged form of the hydrogen-treated AMS-1Cr crystalline chromosilicate, Sample No. 14, was prepared and tested for its ability to isomerize a xylene feed.

A 15-gm portion of Sample No. 14 was cation-exchanged with a solution that had been prepared by dissolving 15 gm of ammonium acetate in 150 ml of distilled $H_2O$. The exchange was carried out for 1.5 hr at a temperature of 95° C. The exchanged sieve was filtered from the exchange solution and washed with approximately 200 ml of distilled $H_2O$. The sieve was allowed to air dry on the filter overnight. This exchange procedure was repeated four times to give a total of five ammonium acetate exchanges. The last exchange was followed with a one-liter distilled-water wash. The washed material was filter dried and then transferred to the forced-draft oven to dry at a temperature of 165° C. overnight.

The dried ammonium form of the crystalline chromosilicate was transferred to a ¾-inch stainless steel tube reactor. The air was purged from the system with a small flow of helium of approximately 1.5 SCFH overnight at a temperature of 300° F. (149° C.). The helium flow was stopped and a hydrogen flow of 3 SCFH was initiated. The temperature was increased at the rate of 100° F. every 30 min until a temperature of 1,000° F. (538° C.) was reached. This temperature was maintained for 4 hr. The hydrogen flow, after the 4 hr, was replaced with a helium flow of about 1.5 SCFH. The temperature controls of the furnace were set to a temperature of 200° F. (93° C.). The furnace cooled via its heat-loss rate which required about 6 hr.

The hydrogen-treated hydrogen form of AMS-1Cr crystalline chromosilicate was then cation-exchanged with 150 ml of a 5% solution of $Ni(NO_3)_2 \cdot 6H_2O$ for 1.5 hr at a temperature of 190° F. (88° C.). The sieve was filtered from the exchange solution, washed with 100 ml of distilled $H_2O$, and filter dried. The sieve was then transferred to a forced-draft drying oven to dry overnight at a temperature of 165° C.

The 13.6 gm of dried, nickel-exchanged crystalline chromosilicate was uniformly dispersed in 84.2 gm of PHF-alumina hydrosol containing 8.7 wt.% solids, obtained from the American Cyanamid Company. A 20-gm quantity of distilled $H_2O$ was added to the sieve to aid dispersion in the hydrosol. The hydrosol plus dispersed sieve was gelled with the addition of 20 ml of a 1-to-1 solution of concentrated ammonium hydroxide in distilled water. The dried sieve was charged to the tube reactor for another hydrogen treatment at a temperature of 1,000° F. (538° C.) for 4 hr using the previously-described procedure. The hydrogen-treated catalyst was crushed and sized to obtain a 30-to-50-mesh material. The 30-to-50-mesh material was charged to the top portion of the tube reactor for a final activation with a hydrogen treatment at a temperature of 1,000° F. (538° C.) for 4 hr, as previously described, with the hydrogen flowing downward in the vertical reactor. This hydrogen-treated catalyst is identified herein after as Catalyst No. 10 and was tested for its ability to isomerize a xylene feed.

A 1-gm portion of Catalyst No. 10 was tested in the same manner as described hereinabove in Example IX. The results of this test, identified hereinafter as Test No. 10, are presented hereinafter in Table XVI. These results indicate that this Catalyst No. 10, containing a nickel-exchanged molecular sieve that had been identified and described as AMS-1Cr crystalline chromosilicate, has selective catalytic activity for xylene isomerization with an appreciable conversion of ethylbenzene to benzene.

TABLE XVI

TEST RESULTS - TEST NO. 10 CATALYST NO. 10

| Cut No. | FD[1] | 8 | 9 |
|---|---|---|---|
| Temperature, °F. | | 800 | 840 |
| Temperature, °C. | | 427 | 449 |
| Product Analysis, wt. % | | | |
| Paraffins & Naphthenes | — | .05 | .04 |
| Benzene | — | .61 | .96 |
| Toluene | .06 | — | .18 |
| Ethylbenzene (EB) | 19.12 | 18.28 | 17.77 |
| p-Xylene (pX) | 9.05 | 14.46 | 16.11 |
| m-Xylene (mX) | 48.25 | 44.83 | 43.68 |
| o-Xylene (oX) | 23.52 | 21.79 | 21.27 |
| $C_9{}^+$ | — | — | — |
| Diethylbenzene | — | — | — |
| Calculated Results | | | |
| $ppH_2$, psia | | 142.0 | 142.7 |
| H/HC | | 6.1 | 6.5 |
| $t_c$, sec. | | 2.67 | 2.60 |
| WHSV, hr$^{-1}$ | | 6.13 | 5.91 |
| pX PATE, % | | 54.2 | 71.3 |
| mX PATE, % | | 58.2 | 74.7 |
| oX PATE, % | | 47.6 | 65.1 |
| EB Conv., % | | 4.4 | 7.1 |
| Time On Oil, hr | | 96 | 113 |
| Cut No. | 10 | 11 | 12 |
| Temperature, °F. | 840 | 840 | 840 |
| Temperature, °C. | 449 | 449 | 449 |

TABLE XVI-continued

TEST RESULTS - TEST NO. 10 CATALYST NO. 10

| Product Analysis, wt. % | | | |
|---|---|---|---|
| Paraffins & Naphthenes | .04 | .09 | |
| Benzene | 1.01 | 1.06 | .96 |
| Toluene | .19 | .21 | .20 |
| Ethylbenzene (EB) | 17.69 | 17.46 | 17.70 |
| p-Xylene (pX) | 16.30 | 16.52 | 15.91 |
| m-Xylene (mX) | 43.61 | 43.55 | 43.92 |
| o-Xylene (oX) | 21.16 | 21.11 | 21.30 |
| $C_9{}^+$ | — | — | — |
| Diethylbenzene | — | — | — |
| Calculated Results | | | |
| $ppH_2$, psia | 142.7 | 142.3 | 140.2 |
| H/HC | 6.5 | 6.3 | 5.7 |
| $t_c$, sec. | 2.61 | 2.60 | 2.56 |
| WHSV, hr$^{-1}$ | 5.90 | 6.03 | 6.70 |
| pX PATE, % | 73.2 | 75.2 | 69.1 |
| mX PATE, % | 75.9 | 77.8 | 71.5 |
| oX PATE, % | 68.3 | 70.5 | 64.8 |
| EB Conv., % | 7.5 | 8.7 | 7.4 |
| Time On Oil, hr | 120 | 185 | 192 |
| Cut No. | 13 | 14 | 15 |
| Temperature, °F. | 840 | 840 | 840 |
| Temperature, °C. | 449 | 449 | 449 |
| Product Analysis, wt. % | | | |
| Paraffins & Naphthenes | — | — | — |
| Benzene | 1.05 | 1.09 | 1.03 |
| Toluene | .20 | .20 | .18 |
| Ethylbenzene (EB) | 17.54 | 17.48 | 17.59 |
| p-Xylene (pX) | 16.51 | 16.54 | 16.33 |
| m-Xylene (mX) | 43.53 | 43.49 | 42.68 |
| o-Xylene (oX) | 21.16 | 21.21 | 20.82 |
| $C_9{}^+$ | — | — | — |
| Diethylbenzene | — | — | — |
| Calculated Results | | | |
| $ppH_2$, psia | 144.8 | 142.0 | 143.1 |
| H/HC | 7.3 | 6.3 | 6.6 |
| $t_c$, sec. | 2.64 | 2.59 | 2.61 |
| WHSV, hr$^{-1}$ | 5.26 | 6.11 | 5.79 |
| pX PATE, % | 75.1 | 75.3 | 76.1 |
| mX PATE, % | 78.3 | 79.3 | 80.2 |
| oX PATE, % | 69.3 | 68.2 | 68.8 |
| EB Conv., % | 8.3 | 8.6 | 8.0 |
| Time On Oil, hr | 208 | 215 | 232 |
| Cut No. | 16 | 17 | 18 | 19 |
| Temperature, °F. | 840 | 880 | 880 | 880 |
| Temperature, °C. | 449 | 471 | 471 | 471 |
| Product Analysis, wt. % | | | | |
| Paraffins & Naphthenes | — | .04 | — | .04 |
| Benzene | 1.11 | 1.75 | 1.78 | 1.80 |
| Toluene | .20 | .33 | .30 | .33 |
| Ethylbenzene (EB) | 17.57 | 16.48 | 17.49 | 16.52 |
| p-Xylene (pX) | 16.56 | 17.87 | 17.65 | 17.74 |
| m-Xylene (mX) | 43.57 | 42.96 | 43.03 | 42.87 |
| o-Xylene (oX) | 20.99 | 20.57 | 20.75 | 20.70 |
| $C_9{}^+$ | — | — | — | — |
| Diethylbenzene | — | — | — | — |
| Calculated Results | | | | |
| $ppH_2$, psia | 141.6 | 143.6 | 141.8 | 142.3 |
| H/HC | 6.1 | 6.8 | 6.2 | 6.3 |
| $t_c$, sec. | 2.59 | 2.54 | 2.51 | 2.52 |
| WHSV, hr$^{-1}$ | 6.23 | 5.61 | 6.19 | 6.04 |
| pX PATE, % | 75.7 | 88.9 | 86.8 | 87.8 |
| mX PATE, % | 77.0 | 86.8 | 86.0 | 87.5 |
| oX PATE, % | 73.4 | 93.1 | 87.9 | 88.5 |
| EB Conv., % | 8.1 | 13.8 | 13.8 | 13.6 |
| Time On Oil, hr | 239 | 256 | 263 | 280 |

[1] FD = Feed

EXAMPLE XVIII

In this example, a catalyst containing a nickel-exchanged form of the hydrogen-treated crystalline chromosilicate and having been impregnated with a nickel nitrate solution was prepared and tested for its ability to isomerize a xylene feed.

A 2-gm portion of Catalyst No. 10 in the form of 30-to-50-mesh material was impregnated with 4 gm of a 5% solution of $Ni(NO_3)_2.6H_2O$ in distilled water. The impregnated material was carefully dried in a forced-draft drying oven with frequent agitation at a temperature of 165° C. for 1 hr and then dried for 4 additional hours at a temperature of 165° C.

The dried impregnated catalyst was transferred to the lower portion of the tube reactor that was used to hydrogen treat the 30-to-50-mesh material in Example XVII. These two materials were placed in the tube at the same time and in such a way as to minimize, if not eliminate, contamination of the original catalyst with the nitrogen oxides produced from the thermally-decomposing nitrate of the impregnated catalyst. Consequently, the placing of the original catalyst above the impregnated catalyst resulted in the flowing hydrogen passing through the original catalyst first. The hydrogen-treated, impregnated material is hereinafter identified as Catalyst No. 11. It was tested for its ability to isomerize a xylene feed and was used in the form of a 30-to-50-mesh material.

A 1-gm portion of Catalyst No. 11 was tested in the same manner as described hereinabove in Example IX. The results of this test, identified hereinafter as Test No. 11, are presented hereinafter in Table XVII.

A comparison of the results obtained from Test No. 11 with those obtained from Test No. 10 shows that the nickel-impregnated catalyst, Catalyst No. 11, has an isomerization activity that is significantly higher than that provided by the non-impregnated catalyst, Catalyst No. 10. This enhanced activity can be attributed to the hydrogenation activity of the impregnated nickel, which minimizes the formation of coke on the alumina matrix material. Such minimal coke production allows increased isomerization to occur on a metal-scavenged alumina surface. It is contemplated that other hydrogenation-dehydrogenation metals or oxides of metals, such as tungsten, molybdenum, cobalt, and the like, will promote the catalytic activity by maintaining a relatively coke-free alumina surface.

The hydrogen-treated AMS-1Cr crystalline chromosilicate provides the X-ray diffraction pattern specified herein and presented in Example XX and has suitable catalytic activity for the conversion of hydrocarbons, e.g., the isomerization of xylenes. Such material has been identified hereinabove as Composition C. Composition C is a crystalline molecular sieve that is designated AMS-1Cr crystalline chromosilicate because: (1) ion-exchange dictates that chromium has replaced aluminum of typical crystalline aluminosilicates; (2) no $Cr_2O_3$ was detected in the sieve that has been treated with hydrogen at elevated temperatures; and (3) a 3-fold increase in chromium concentration in the chromosilicate sieve provides a pronounced shoulder on the 3.85 Å reflection. Composition C can be converted to Composition B by a calcination in air to yield a crystalline chromosilicate and a chromia phase. Composition C, as an AMS-1Cr crystalline chromosilicate molecular sieve, has an acidic character in the hydrogen form which catalyzes the isomerization of xylenes. In addition, the activity for the isomerization of xylenes is enhanced by the impregnation of the chromosilicate with nickel or another hydrogenation-dehydrogenation metal.

TABLE XVII

TEST RESULTS - TEST NO. 11
CATALYST NO. 11

| Cut No. | FD[1] | 1 | 3 | 4 | 5 | 6 | 7 | 9 | 10 | 11 | 12 | 13 | 14 |
|---|---|---|---|---|---|---|---|---|---|---|---|---|---|
| Temperature, °F. | | 600 | 640 | 680 | 720 | 760 | 800 | 800 | 800 | 800 | 800 | 840 | 840 |
| Temperature, °C. | | 316 | 338 | 360 | 382 | 404 | 427 | 427 | 427 | 427 | 427 | 449 | 449 |
| Product Analysis, wt. % | | | | | | | | | | | | | |
| Paraffins & Naphthenes | | — | — | — | .03 | — | — | — | — | — | — | .05 | .05 |
| Benzene | — | .08 | .09 | .20 | .33 | .53 | 1.00 | .93 | .90 | .81 | .73 | 1.35 | 1.45 |
| Toluene | .06 | .11 | .09 | .10 | .11 | .13 | .20 | .19 | .20 | .15 | .14 | .22 | .26 |
| Ethylbenzene (EB) | 19.12 | 19.07 | 18.96 | 18.93 | 18.71 | 18.34 | 17.69 | 17.87 | 17.94 | 18.09 | 18.07 | 17.23 | 17.07 |
| p-Xylene (pX) | 9.05 | 9.88 | 10.58 | 11.97 | 14.06 | 15.53 | 17.43 | 17.15 | 16.89 | 16.12 | 15.65 | 17.63 | 17.77 |
| m-Xylene (mX) | 48.25 | 47.68 | 47.25 | 46.26 | 44.91 | 43.99 | 42.98 | 43.16 | 43.25 | 43.70 | 44.03 | 42.90 | 42.87 |
| o-Xylene (oX) | 23.52 | 23.18 | 23.03 | 22.55 | 21.86 | 21.48 | 20.70 | 20.63 | 20.88 | 21.13 | 21.39 | 20.62 | 20.53 |
| $C_9{}^+$ | — | — | — | — | — | — | — | — | — | — | — | — | — |
| Diethylbenzene | — | — | — | — | — | — | — | — | — | — | — | — | — |
| Calculated Results | | | | | | | | | | | | | |
| $ppH_2$, psia | | 143.0 | 144.5 | 145.2 | 147.3 | 148.2 | 144.5 | 145.5 | 142.0 | 128.9 | 138.6 | 149.0 | 145.6 |
| H/HC | | 6.6 | 7.2 | 7.5 | 8.5 | 9.0 | 7.2 | 7.6 | 6.2 | 3.6 | 5.3 | 9.5 | 7.6 |
| $t_c$, sec. | | 3.20 | 3.12 | 3.02 | 2.96 | 2.88 | 2.72 | 2.74 | 2.67 | 2.43 | 2.61 | 2.72 | 2.66 |
| WHSV, $hr^{-1}$ | | 5.80 | 5.34 | 5.13 | 4.51 | 4.26 | 5.34 | 5.01 | 6.13 | 10.61 | 7.22 | 4.03 | 5.01 |
| pX PATE, % | | 8.24 | 15.0 | 29.0 | 50.0 | 64.7 | 84.1 | 81.6 | 78.8 | 71.2 | 66.2 | 86.5 | 87.9 |
| mX PATE, % | | 10.23 | 19.2 | 35.4 | 58.2 | 73.4 | 88.6 | 84.2 | 83.5 | 75.5 | 71.2 | 87.9 | 88.5 |
| oX PATE, % | | 6.22 | 10.4 | 21.13 | 38.9 | 51.9 | 76.5 | 77.2 | 71.2 | 64.1 | 58.1 | 84.1 | 86.7 |
| EB Conv., % | | .26 | 0.84 | .99 | 2.1 | 4.1 | 7.5 | 6.2 | 6.5 | 5.4 | 5.5 | 9.9 | 10.7 |
| Time On Oil, hr | | 17 | 41 | 48 | 65 | 72.25 | 89.0 | 113.0 | 120.0 | 185.0 | 190.0 | 206.0 | 213.0 |

| | Cut No. | 15 | 16 | 17 | 18 | 19 |
|---|---|---|---|---|---|---|
| | Temperature, °F. | 840 | 840 | 880 | 880 | 880 |
| | Temperature, °C. | 449 | 449 | 471 | 471 | 471 |
| | Product Analysis, wt. % | | | | | |
| | Paraffins & Naphthenes | .03 | .02 | .01 | .01 | .01 |
| | Benzene | 1.30 | 1.17 | 1.50 | 1.73 | 1.78 |
| | Toluene | .26 | .23 | .35 | .36 | .37 |
| | Ethylbenzene (EB) | 16.68 | 16.90 | 15.83 | 15.73 | 15.83 |
| | p-Xylene (pX) | 17.89 | 17.72 | 18.57 | 18.53 | 18.51 |
| | m-Xylene (mX) | 42.70 | 42.85 | 42.67 | 42.54 | 42.59 |
| | o-Xylene (oX) | 20.51 | 20.57 | 20.36 | 20.32 | 20.18 |
| | $C_9{}^+$ | .65 | .54 | .76 | .78 | .73 |
| | Diethylbenzene | .41 | .34 | .36 | .38 | .35 |

TABLE XVII-continued
TEST RESULTS - TEST NO. 11
CATALYST NO. 11

| Calculated Results | | | | | |
|---|---|---|---|---|---|
| ppH$_2$, psia | 142.2 | 140.2 | 143.6 | 142.7 | 143.8 |
| H/HC | 6.3 | 5.7 | 6.8 | 6.5 | 6.9 |
| t$_c$, sec. | 2.60 | 2.56 | 2.54 | 2.53 | 2.55 |
| WHSV, hr$^{-1}$ | 6.05 | 6.69 | 5.62 | 5.91 | 5.55 |
| pX PATE, % | 89.3 | 87.4 | 95.2 | 95.6 | 95.7 |
| mX PATE, % | 90.6 | 88.6 | 92.5 | 93.2 | 91.5 |
| oX PATE, % | 86.8 | 85.3 | 100.3 | 100.5 | 103.8 |
| EB Conv., % | 12.8 | 11.6 | 17.2 | 17.7 | 17.2 |
| Time On Oil, hr | 230.0 | 237.0 | 254.0 | 261.0 | 278.0 |

[1] FD = Feed

EXAMPLE XIX

The X-ray diffraction pattern for the Sample No. 11 AMS-1Cr chromosilicate of Example VIII was found to be:

TABLE XVIII

| Interplanar Spacing d, Å | I/I$_o$ | Assigned Strength |
|---|---|---|
| 11.14 ± 0.2 | 33 | M |
| 9.89 ± 0.2 | 100 | VS |
| 6.71 ± 0.2 | 4 | VW |
| 6.35 ± 0.1 | 6 | VW |
| 5.99 ± 0.1 | 10 | W |
| 5.71 ± 0.1 | 7 | VW |
| 5.58 ± 0.1 | 7 | VW |
| 5.34 ± 0.1 | 3 | VW |
| 4.97 ± 0.1 | 20 | M |
| 4.61 ± 0.08 | 3 | VW |
| 4.36 ± 0.08 | 5 | VW |
| 4.26 ± 0.08 | 8 | VW |
| 4.07 ± 0.08 | 6 | VW |
| 4.01 ± 0.08 | 3 | VW |
| 3.85 ± 0.07 | 47 | MS |
| 3.81 ± 0.07 | 37 | M |
| 3.72 ± 0.05 | 26 | M |
| 3.63 ± 0.05 | 32 | M |
| 3.57 ± 0.05 | 3 | VW |
| 3.49 ± 0.05 | 3 | VW |
| 3.43 ± 0.05 | 5 | VW |
| 3.35 ± 0.05 | 7 | VW |
| 3.31 ± 0.05 | 13 | W |
| 3.25 ± 0.05 | 2 | VW |
| 3.17 ± 0.05 | 3 | VW |
| 3.05 ± 0.03 | 4 | VW |
| 3.04 ± 0.03 | 4 | VW |
| 2.99 ± 0.02 | 10 | W |
| 2.95 ± 0.02 | 8 | VW |
| 2.90 ± 0.02 | 3 | VW |
| 2.74 ± 0.02 | 5 | VW |
| 2.67 ± 0.02 | 35 | M |
| 2.48 ± 0.02 | 38 | M |
| 2.43 ± 0.02 | 3 | VW |
| 2.27 ± 0.02 | 2 | VW |
| 2.20 ± 0.02 | 2 | VW |
| 2.17 ± 0.02 | 13 | W |
| 2.04 ± 0.02 | 3 | VW |
| 2.01 ± 0.02 | 6 | VW |
| 1.99 ± 0.02 | 16 | W |
| 1.82 ± 0.02 | 13 | W |
| 1.76 ± 0.02 | 4 | VW |
| 1.67 ± 0.02 | 32 | M |

Please note that this has a higher chromium concentration than the sample which provided the X-ray diffraction pattern exhibited in Table I hereinabove. The increased amount of chromium that was on the sieve framework caused a shift in some d spacings, for example, 11.04 was shifted to 11.14 and 10.04 to 9.89, and a change in some relative intensities, for example, the corresponding relative intensities changed from 100 to 33 and 68 to 100, respectively.

The importance of the 2.67 and 2.48 interplanar spacings is in direct proportion to the chromium concentration in the sieve framework prior to the air-treatment.

The stronger peaks for this air-treated AMS-1Cr crystalline chromosilicate are presented hereinbelow in Table XIX.

TABLE XIX

| Interplanar Spacing d, Å | I/I$_o$ | Assigned Strength |
|---|---|---|
| 11.14 ± 0.2 | 33 | M |
| 9.89 ± 0.02 | 100 | VS |
| 3.85 ± 0.07 | 47 | MS |
| 3.81 ± 0.07 | 37 | M |
| 3.72 ± 0.05 | 26 | M |
| 3.63 ± 0.05 | 32 | M |
| 2.67 ± 0.02 | 35 | M |
| 2.48 ± 0.02 | 38 | M |

EXAMPLE XX

The X-ray diffraction pattern for the Sample No. 14 AMS-1Cr chromosilicate of Example XV was found to be:

TABLE XX

| Interplanar Spacing d, Å | I/I$_o$ | Assigned Strength |
|---|---|---|
| 11.15 ± 0.02 | 11 | W |
| 9.96 ± 0.2 | 100 | VS |
| 9.03 ± 0.2 | 0.4 | VW |
| 7.48 ± 0.2 | 0.6 | VW |
| 7.09 ± 0.2 | 0.4 | VW |
| 6.72 ± 0.2 | 0.6 | VW |
| 6.36 ± 0.1 | 1.2 | VW |
| 5.99 ± 0.1 | 6 | VW |
| 5.71 ± 0.1 | 6 | VW |
| 5.56 ± 0.1 | 2 | VW |
| 5.36 ± 0.1 | 0.4 | VW |
| 4.97 ± 0.1 | 17 | W |
| 4.62 ± 0.08 | 0.7 | VW |
| 4.47 ± 0.08 | 0.6 | VW |
| 4.36 ± 0.08 | 0.6 | VW |
| 4.26 ± 0.08 | 2 | VW |
| 4.01 ± 0.08 | 2 | VW |
| 3.85 ± 0.07 | 29 | M |
| 3.82 ± 0.07 | 48 | MS |
| 3.75 ± 0.05 | 23 | M |
| 3.44 ± 0.05 | 2 | VW |
| 3.35 ± 0.05 | 2 | VW |
| 3.32 ± 0.05 | 9 | VW |
| 3.25 ± 0.05 | 1 | VW |
| 3.18 ± 0.05 | 0.4 | VW |
| 3.06 ± 0.03 | 2 | VW |
| 3.05 ± 0.03 | 2 | VW |
| 2.99 ± 0.02 | 3 | VW |
| 2.95 ± 0.02 | 2 | VW |
| 2.86 ± 0.02 | 0.4 | VW |
| 2.79 ± 0.02 | 1 | VW |
| 2.73 ± 0.02 | 0.9 | VW |
| 2.61 ± 0.02 | 1 | VW |
| 2.56 ± 0.02 | 0.4 | VW |

TABLE XX-continued

| Interplanar Spacing d, Å | I/I$_o$ | Assigned Strength |
|---|---|---|
| 2.52 ± 0.02 | 1 | VW |
| 2.49 ± 0.02 | 4 | VW |
| 2.42 ± 0.02 | 0.9 | VW |
| 2.39 ± 0.02 | 0.9 | VW |
| 2.32 ± 0.02 | 0.4 | VW |
| 2.20 ± 0.02 | 0.7 | VW |
| 2.17 ± 0.02 | 0.5 | VW |
| 2.01 ± 0.02 | 3 | VW |
| 1.99 ± 0.02 | 12 | W |
| 1.95 ± 0.02 | 0.9 | VW |
| 1.91 ± 0.02 | 0.9 | VW |
| 1.88 ± 0.02 | 0.5 | VW |
| 1.86 ± 0.02 | 0.4 | VW |

The stronger peaks for this hydrogen-treated AMS-1Cr crystalline chromosilicate are presented hereinbelow in Table XXI:

TABLE XXI

| Interplanar Spacing d, Å | I/I$_o$ | Assigned Strength |
|---|---|---|
| 11.15 ± 0.2 | 11 | W |
| 9.96 ± 0.2 | 100 | VS |
| 5.99 ± 0.1 | 6 | VW |
| 5.71 ± 0.1 | 6 | VW |
| 4.97 ± 0.1 | 17 | W |
| 3.85 ± 0.07 | 29 | M |
| 3.82 ± 0.07 | 48 | MS |
| 3.75 ± 0.05 | 23 | M |
| 3.32 ± 0.05 | 9 | VW |
| 1.99 ± 0.02 | 12 | W |

As shown hereinabove, a catalytically active material can be obtained when the heat treatment is carried out in either a hydrogen atmosphere or an oxygen-containing atmosphere. Composition C will result if hydrogen is employed; Composition B will result if an oxygen-containing atmosphere is used.

EXAMPLE XXI

An AMS-1CR crystalline chromosilicate was prepared in a manner similar to that described hereinabove. The quantities of reactants used in this chromosilicate preparation are presented hereinbelow in Table XXII. The amount of chromium that was employed in the preparation of this crystalline chromosilicate provided a "chromium factor" of "X3".

TABLE XXII

| REACTANTS FOR CHROMOSILICATE PREPARATION | | |
|---|---|---|
| Reactant | Wt, gm | pH |
| Distilled H$_2$O | 800.0 | — |
| Cr$_2$(SO$_4$)$_3$.xH$_2$O | 28.8 | — |
| NaOH | 17.0 | 11.1 |
| Tetrapropylammonium Bromide | 124.8 | — |
| Ludox, HS-40 | 127.2 | 10.2 |

The pH of the mixture subsequent to the addition of a particular reactant is presented in Table XXII. The total solution was stirred vigorously and was placed in a crystallization vessel, which was sealed and subsequently placed in a forced-draft oven. The composite was heated in the vessel at a temperature of 329° F. (165° C.) for 7 days.

After 7 days, the crystallization vessel was taken from the oven and cooled. The contents were removed from the vessel, filtered, and washed with distilled water. After being dried in air for a period of time, the composite was placed in the forced-draft oven and dried overnight (approximately 16 hours) at a temperature of 329° F. (165° C.).

The dried composite was then treated in hydrogen for 4 hours. The temperature was raised from 200° F. (93° C.) to a value approximately 1,000° F. (538° C.) over a period of 4 hours and then held at that temperature for 4 hours, while hydrogen was being passed over the composite.

An X-ray diffraction pattern for the hydrogen-treated material was obtained in a manner similar to that described hereinabove. The interplanar spacings (d-spacings), associated peak heights, and relative intensities (I/I$_o$) are presented in Table XXIII hereinbelow.

TABLE XXIII

| X-RAY DATA FOR AMS-1Cr(X3) SAMPLE | | | | | |
|---|---|---|---|---|---|
| d, Å | Peak Height | I/I$_o$ | d, Å | Peak Height | I/I$_o$ |
| 11.09 | 57.5 | 46 | 2.95 | 16.0 | 13 |
| 10.00 | 77.5 | 62 | 2.92 | 4.0 | 3 |
| 9.89 | 118 | 94 | 2.86 | 5.5 | 4 |
| 6.67 | 7 | 6 | 2.78 | 4.0 | 3 |
| 6.34 | 11 | 9 | 2.73 | 9.0 | 7 |
| 5.98 | 21 | 17 | 2.61 | 7.0 | 6 |
| 5.92 | 9 | 7 | 2.59 | 7.0 | 6 |
| 5.69 | 13 | 10 | 2.55 | 5.5 | 4 |
| 5.56 | 12 | 10 | 2.51 | 9.0 | 7 |
| 5.36 | 3.5 | 3 | 2.48 | 14.5 | 12 |
| 5.02 | 10 | 8 | 2.47 | 7.0 | 6 |
| 4.96 | 24 | 19 | 2.42 | 7.5 | 6 |
| 4.61 | 6 | 5 | 2.39 | 7.5 | 6 |
| 4.35 | 10 | 8 | 2.01 | 27.0 | 22 |
| 4.25 | 15 | 12 | 2.00 | 17.0 | 14.0 |
| 4.07 | 6 | 5 | 1.99 | 38.0 | 30.0 |
| 3.85 | 125 | 100 | 1.98 | 22.0 | 18 |
| 3.81 | 86 | 69 | 1.95 | 7.0 | 6 |
| 3.74 | 48 | 38 | 1.91 | 7.5 | 6 |
| 3.71 | 58 | 46 | 1.88 | 6.0 | 5 |
| 3.65 | 19 | 15 | 1.86 | 5.0 | 4 |
| 3.62 | 18 | 14 | | | |
| 3.44 | 9.5 | 8 | | | |
| 3.39 | 3.5 | 3 | | | |
| 3.35 | 11.5 | 9 | | | |
| 3.31 | 19 | 15 | | | |
| 3.25 | 6 | 5 | | | |
| 3.05 | 11.5 | 9 | | | |
| 2.99 | 29.0 | 23 | | | |

In Table XXIII, d-spacings having relatively strong intensities are found at 10.00 Å and 9.89 Å. These are represented as a large peak at 9.89 Å and a smaller peak at 10.00 Å, the latter appearing as a shoulder connected to the larger peak.

This combination of peaks, i.e., a 9.89 Å peak having as a shoulder the 10.00 Å peak, is not characteristic of other molecular sieve materials, e.g., ZSM-5 crystalline aluminosilicates, AMS-1B crystalline borosilicates, and crystalline metal organosilicates. Consequently, it appears to represent a different crystalline framework, suggesting a unique molecular sieve material.

What is claimed is:

1. A catalytic composition which comprises a mixture of a crystalline chromosilicate and an oxide of chromium, said catalytic composition providing an X-ray diffraction pattern comprising the following X-ray diffraction lines and assigned strengths:

| Interplanar Spacing d, Å | Assigned Strength |
|---|---|
| 11.14 ± 0.2 | M |
| 9.89 ± 0.2 | VS |
| 3.85 ± 0.07 | MS |

| Interplanar Spacing d, Å | Assigned Strength |
|---|---|
| 3.81 ± 0.07 | M |
| 3.72 ± 0.05 | M |
| 3.63 ± 0.05 | M |
| 2.67 ± 0.02 | M |
| 2.48 ± 0.02 | M | and having the following composition in terms of mole ratios of oxides:

0.9±0.2 $M_{2/n}O:Cr_2O_3:YSiO_2:ZH_2O$, wherein M is at least one cation having a valence of n, Y is a value within the range of about 4 to about 500, and Z is a value within the range of 0 to about 160.

2. The catalytic composition of claim 1, wherein said M is selected from the group consisting of hydrogen ions, metal ions, and mixtures thereof.

3. The catalytic composition of claim 1, wherein the value of Y is within the range of about 4 to about 200.

4. The catalytic composition of claim 1, wherein the value of Z is within the range of about 0 to about 40.

5. The catalytic composition of claim 1, wherein said catalytic composition has been prepared by the method which comprises: (1) preparing a mixture containing an oxide of silicon, a compound of chromium, a hydroxide of an alkali metal or an alkaline earth metal, an alkylammonium cation or a precursor of an alkylammonium cation, and water; (2) maintaining said mixture at suitable reaction conditions to affect formation of a crystalline material, said reaction conditions comprising a reaction temperature within the range of about 25° C. to about 300° C., a pressure of at least the vapor pressure of water at the reaction temperature, and a reaction time that is sufficient to effect crystallization to crystals of said chromosilicate; (3) washing and drying said crystals; and (4) calcining the resulting product in an oxygen-containing atmosphere at a temperature within the range of about 800° F. (427° C.) to about 1,700° F. (927° C.).

6. The catalytic composition of claim 2, wherein M comprises nickel ions and hydrogen ions.

7. The catalytic composition of claim 3, wherein the value of Z is within the range of about 0 to about 40.

8. The catalytic composition of claim 6, wherein M comprises nickel ions.

9. The catalytic composition of claim 7, wherein the value of Y is within the range of about 4 to about 40.

10. A method for preparing a catalytic composition, which method comprises: (1) preparing a mixture containing an oxide of silicon, a compound of chromium, a hydroxide of an alkali metal or an alkaline earth metal, an alkylammonium cation or a precursor of an alkylammonium cation, and water; (2) maintaining said mixture at suitable reaction conditions to effect formation of a crystalline material, said reaction conditions comprising a reaction temperature within the range of about 25° C. to about 300° C., a pressure of at least the vapor pressure of water at the reaction temperature, and a reaction time that is sufficient to effect crystallization to crystals of said chromosilicate; (3) washing and drying said crystals; and (4) calcining the resulting product in an oxygen-containing atmosphere at a temperature within the range of about 800° F. (427° C.) to about 1,700° F. (927° C.).

11. The method of claim 10, wherein said compound of chromium is $Cr_2(SO_4)_3.XH_2O$ or $Cr(C_2H_3O_2)_3.H_2O$.

12. The method of claim 10, wherein said mixture contains reactants in the following mole ratios of oxides of the reactants:

| | |
|---|---|
| $SiO_2/Cr_2O_3$ | 1–500 |
| $R_4N^+/(R_4N^+ + Na^+)$ | 0.1–1 |
| $OH^-/SiO_2$ | 0.1–10 |
| $H_2O/OH^-$ | 10–500 | wherein R is alkyl and $Na^+$ is sodium, any other alkali metal, or an alkaline earth metal.

13. The method of claim 11, wherein said reaction temperature is within the range of about 150° C. to about 180° C.

14. The method of claim 12, wherein said compound of chromium is $Cr_2(SO_4)_3.XH_2O$ or $Cr(C_2H_3O_2)_3.H_2O$.

15. The method of claim 12, wherein said reaction temperature is within the range of about 150° C. to about 180° C.

16. The method of claim 14, wherein said reaction temperature is within the range of about 150° C. to about 180° C.

* * * * *

UNITED STATES PATENT OFFICE
CERTIFICATE OF CORRECTION

Patent No. 4,405,504      Dated SEPTEMBER 20, 1983

Inventor(s) MARVIN R. KLOTZ

It is certified that error appears in the above-identified patent and that said Letters Patent are hereby corrected as shown below:

| | |
|---|---|
| Column 2, line 16, | "2,882,234" should be --2,882,243--. |
| Column 26, line 45, | "2.65 A" should be --2.65 A--. |
| Column 40, line 41, | "11.15 ± 0.02" should be --11.15 ± 0.2--. |
| Column 44, line 41, | "toabout should be --to about--. |

Signed and Sealed this

Eleventh Day of September 1984

[SEAL]

Attest:

GERALD J. MOSSINGHOFF

Attesting Officer     Commissioner of Patents and Trademarks